United States Patent [19]

Eppstein et al.

[11] Patent Number: 5,545,412
[45] Date of Patent: Aug. 13, 1996

[54] N-[1, (1-1)-DIALKYLOXY]-AND N-[1, (1-1)-DIALKENYLOXY]-ALK-1-YL-N,N,N-TETRASUBSTITUTED AMMONIUM LIPIDS AND USES THEREFOR

[75] Inventors: Deborah A. Eppstein, Menlo Park; Philip L. Felgner, Los Altos; Thomas R. Gadek, Oakland; Gordon H. Jones, Cupertino, all of Calif.; Richard B. Roman, Fairhope, Ala.

[73] Assignee: Syntex (U.S.A.) Inc., Palo Alto, Calif.

[21] Appl. No.: 415,962

[22] Filed: Apr. 3, 1995

Related U.S. Application Data

[62] Division of Ser. No. 237,807, May 4, 1994, which is a division of Ser. No. 15,738, Feb. 10, 1993, Pat. No. 5,366,737, which is a division of Ser. No. 614,412, Nov. 16, 1990, Pat. No. 5,208,036, which is a division of Ser. No. 524,257, May 15, 1990, Pat. No. 5,049,386, which is a division of Ser. No. 428,815, Oct. 27, 1989, Pat. No. 4,946,787, which is a division of Ser. No. 114,809, Oct. 29, 1987, Pat. No. 4,897,355, which is a continuation-in-part of Ser. No. 877,916, Jun. 24, 1986, abandoned, which is a continuation-in-part of Ser. No. 689,407, Jan. 7, 1985, abandoned.

[51] Int. Cl.[6] ............... A61K 9/127; A61K 9/70; A61F 2/02; B01J 13/02
[52] U.S. Cl. ............ 424/450; 424/423; 424/427; 424/428; 424/449; 435/829; 264/4.1; 264/4.33; 264/4.6
[58] Field of Search ............... 424/423, 427, 424/428, 449, 450; 435/829; 264/4.1, 4.33, 4.6

[56] References Cited

U.S. PATENT DOCUMENTS

| | | | |
|---|---|---|---|
| 2,666,783 | 11/1954 | Lytton | 560/250 |
| 3,231,509 | 1/1966 | Shama | 514/643 |
| 3,272,712 | 9/1966 | Kalopissis et al. | 424/70 |
| 3,337,628 | 8/1967 | Crowther et al. | 564/349 |
| 3,415,873 | 12/1968 | Stevens | 562/467 |
| 3,432,545 | 3/1969 | Howe | 560/106 |
| 3,445,440 | 5/1969 | Susi et al. | 524/156 |
| 3,459,782 | 8/1969 | Koppe et al. | 558/408 |
| 3,534,084 | 10/1970 | Narayanan et al. | 560/252 |
| 3,534,085 | 10/1970 | Narayanan et al. | 560/252 |
| 3,534,086 | 10/1970 | Narayanan et al. | 560/252 |
| 3,538,150 | 11/1970 | Gilman et al. | 562/597 |

(List continued on next page.)

FOREIGN PATENT DOCUMENTS

| | | |
|---|---|---|
| 904536 | 7/1986 | Belgium. |
| 0037780 | 10/1981 | European Pat. Off.. |
| 2008578 | 6/1979 | United Kingdom. |

OTHER PUBLICATIONS

Nicolau et al., "In vivo expression of rat insulin after intravenous administration of liposome–entrapped gene for rat insulin I," *Proc Natl. Acad. Sci. USA*, 80, 1068–1072 (1983).

J. Antibact. Antifung. Agents vol. 10, No. 9 pp. 377–381, 1982.

Kawamata et al, *Chemical Abstracts*, vol. 92, No. 11643175, (1980).

Primary Examiner—Carlos Azpuru
Attorney, Agent, or Firm—Heller Ehrman White & McAuliffe

[57] ABSTRACT

This invention relates to compounds of the formula

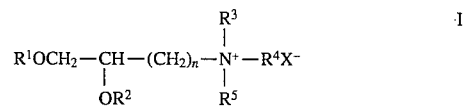

or an optical isomer thereof wherein $R^1$ and $R^2$ are the same or different and are an alkyl or alkenyl group of 6 to 24 carbon atoms; $R^3$, $R^4$ and $R^5$ are the same or different and are alkyl of 1 to 8 carbon atoms, aryl, aralkyl of 7 to 11 carbon atoms, or when two or three of $R^3$, $R^4$, and $R^5$ are taken together to form quinuclidino, piperidino, pyrrolidino, or morpholino, n is 1 to 8; and X is a pharmaceutically acceptable anion.

4 Claims, 3 Drawing Sheets

U.S. PATENT DOCUMENTS

| | | | |
|---|---|---|---|
| 3,567,729 | 3/1971 | Lewis et al. | 564/292 |
| 3,574,755 | 4/1971 | McConnell et al. | 564/292 |
| 3,646,066 | 2/1972 | Narayanan et al. | 560/252 |
| 3,646,067 | 2/1972 | Narayanan et al. | 560/252 |
| 3,712,927 | 11/1973 | Howe et al. | 560/46 |
| 3,932,495 | 1/1976 | Murtussen et al. | 564/292 |
| 3,972,855 | 8/1976 | Martinsson et al. | 558/38 |
| 4,040,992 | 8/1977 | Bechara et al. | 521/117 |
| 4,137,180 | 1/1979 | Naik et al. | 252/8.8 |
| 4,166,132 | 8/1979 | Kraska | 514/668 |
| 4,193,999 | 3/1980 | Kraska | 514/331 |
| 4,194,006 | 3/1980 | Cavazza | 514/546 |
| 4,196,217 | 4/1980 | Rencurel et al. | 564/292 |
| 4,199,565 | 4/1980 | Fullerton | 424/89 |
| 4,201,767 | 5/1980 | Fullerton et al. | 424/89 |
| 4,215,146 | 7/1980 | Kraska | 514/655 |
| 4,235,871 | 11/1980 | Papahadjopoulos et al. | 424/450 |
| 4,235,877 | 11/1980 | Fullerton | 424/89 |
| 4,238,373 | 12/1980 | Hardy et al. | 564/292 |
| 4,255,449 | 3/1981 | Cavazza | 514/554 |
| 4,259,217 | 3/1981 | Murphy | 564/292 |
| 4,261,975 | 4/1981 | Fullerton et al. | 424/89 |
| 4,262,021 | 4/1981 | Kraska | 514/631 |
| 4,358,368 | 11/1982 | Hellsten et al. | 209/167 |
| 4,362,719 | 12/1982 | Cavazza | 514/4 |
| 4,394,448 | 7/1983 | Szoka, Jr. et al. | 424/450 |
| 4,439,438 | 3/1984 | Cavazza | 514/357 |
| 4,443,475 | 4/1984 | Cavazza | 514/547 |
| 4,485,054 | 11/1984 | Mezei et al. | 264/4.6 |
| 4,522,803 | 6/1985 | Lenk et al. | 424/1.1 |
| 4,897,355 | 1/1990 | Eppstein et al. | 435/240.2 |

N-[1, (1-1)-DIALKYLOXY]-AND N-[1, (1-1)-DIALKENYLOXY]-ALK-1-YL-N,N,N-TETRASUBSTITUTED AMMONIUM LIPIDS AND USES THEREFOR

BACKGROUND OF THE INVENTION

1. Related Applications

This is a division of application Ser. No. 08/237,807, filed May 5, 1994, which is a division of Ser. No. 08/015,738, filed Feb. 10, 1993, now U.S. Pat. No. 5,366,737; which is a division of Ser. No. 07/614,412, filed Nov. 16, 1990, now U.S. Pat. No. 5,208,036; which is a division of Ser. No. 07/524,257, filed May 15, 1990, now U.S. Pat. No. 5,049,386; which is a division of Ser. No. 07/428,815, filed Oct. 27, 1989, now U.S. Pat. No. 4,946,787; which is a divisoin of Ser. No. 07/114,809, filed Oct. 29, 1987, now U.S. Pat. No. 4,897,355; which is a continuation-in-part of Ser. No. 06/877,916, filed Jun. 24, 1986, now abandoned; which is a continuation-in-part of Ser. No. 06/689,407, filed Jan. 7, 1985, now abandoned.

2. Field of the Invention

This invention relates to lipophilic cationic compounds and several of their uses. The invention also relates to a novel DNA transfection method, in which the compounds of this invention can be used.

3. Related Art

Liposomes are microscopic vesicles consisting of concentric lipid bilayers. Structurally, liposomes range in size and shape from long tubes to spheres, with dimensions from a few hundred Angströms to fractions of a millimeter. Regardless of the overall shape, the bilayers are generally organized as closed concentric lamellae, with an aqueous layer separating each lamella from its neighbor. Vesicle size normally falls in a range of between about 20 and about 30,000 nm in diameter. The liquid film between lamellae is usually between about 3 and 10 nm.

Typically, liposomes can be divided into three categories based on their overall size and the nature of the lamellar structure. The three classifications, as developed by the New York Academy Sciences Meeting, "Liposomes and Their Use in Biology and Medicine," of December 1977, are multi-lamellar vesicles (MLV's), small uni-lamellar vesicles (SUV's) and large uni-lamellar vesicles (LUV's).

SUV's range in diameter from approximately 20 to 50 nm and consist of a single lipid bilayer surrounding an aqueous compartment. Unilamellar vesicles can also be prepared in sizes from about 50 nm to 600 nm in diameter. While unilamellar are single compartmental vesicles of fairly uniform size, MLV's vary greatly in size up to 10,000 nm, or thereabouts, are multi-compartmental in their structure and contain more than one bilayer. LUV liposomes are so named because of their large diameter which ranges from about 600 nm to 30,000 nm; they can contain more than one bilayer.

Liposomes may be prepared by a number of methods not all of which produce the three different types of liposomes. For example, ultrasonic dispersion by means of immersing a metal probe directly into a suspension of MLV's is a common way for preparing SUV's.

Preparing liposomes of the MLV class usually involves dissolving the lipids in an appropriate organic solvent and then removing the solvent under a gas or air stream. This leaves behind a thin film of dry lipid on the surface of the container. An aqueous solution is then introduced into the container with shaking in order to free lipid material from the sides of the container. This process disperses the lipid, causing it to form into lipid aggregates or liposomes.

Liposomes of the LUV variety may be made by slow hydration of a thin layer of lipid with distilled water or an aqueous solution of some sort.

Alternatively, liposomes may be prepared by lyophilization. This process comprises drying a solution of lipids to a film under a stream of nitrogen. This film is then dissolved in a volatile solvent, frozen, and placed on a lyophilization apparatus to remove the solvent. To prepare a pharmaceutical formulation containing a drug, a solution of the drug is added to the lyophilized lipids, whereupon liposomes are formed.

A variety of methods for preparing various liposome forms have been described in the periodical and patent literature. For specific reviews and information on liposome formulations, reference is made to reviews by Pagano and Weinstein (*Ann. Rev. Biophysic. Bioeng.*, 7, 435–68 (1978)) and Szoka and Papahadjopoulos (*Ann. Rev. Biophysic. Bioeng.*, 9, 467–508 (1980)) and additionally to a number of patents, for example, U.S. Pat. Nos. 4,229,360; 4,224,179; 4,241,046; 4,078,052; and 4,235,871.

Thus, in the broadest terms, liposomes are prepared from one or more lipids. Though it has been thought that any type of lipid could be used in liposomes, e.g. cationic, neutral or anionic lipids, experience with positively charged liposomes has indicated several problems which have not been fully addressed to date. The amines which have to date been employed in preparing cationic liposomes have either not been sufficiently chemically stable to allow for the storage of the vesicle itself (short shelf life) or the structure of the amines has been such that they can be leached out of the liposome bilayer. One such amine, stearylamine, has toxicity concerns which limit its use as a component of liposomes in a pharmaceutical formulation. Another amine, dimethyl dioctadecyl ammonium bromide, lacks the appropriate molecular geometry for optimum formation of the bilayers that comprise the liposome structure.

Various biological substances have been encapsulated into liposomes by contacting a lipid with the matter to be encapsulated and then forming the liposomes as described above. A drawback of this methodology, commonly acknowledged by those familiar with the art, is that the fraction of material encapsulated into the liposome structure is generally less than 50%, usually less than 20%, often necessitating an extra step to remove unencapsulated material. An additional problem, related to the above, is that after removal of unencapsulated material, the encapsulated material can leak out off the liposome. This second issue represents a substantial stability problem to which such attention has been addressed in the art.

Liposomes have been used to introduce DNA into cells. More specifically, various DNA transfection methodologies have been used, including microinjection, protoplast fusion, liposome fusion, calcium phosphate precipitation, electroporation and retroviruses. All of these methods suffer from some significant drawbacks: they tend to be too inefficient, too toxic, too complicated or too tedious to be conveniently and effectively adapted to biological and/or therapeutic protocols on a large scale. For instance, the calcium phosphate precipitation method can successfully transfect only about 1 in $10^7$ to 1 in $10^4$ cells; this frequency is too low to be applied to current biological and/or therapeutic protocols. Microinjection is efficient but not practical for large numbers of cells or for large numbers of patients. Protoplast fusion is more efficient than the calcium phosphate method but the propylene glycol that is required is toxic to the cells. Electroporation is more efficient then calcium phosphate but requires a special apparatus. Retroviruses are sufficiently efficient but the introduction of viruses into the patient leads to concerns about infection and cancer. Liposomes have been used before but the published protocols have not been shown to be any more efficient than calcium phosphate. The most desirable transfection method would involve one that gives very high efficiency without the introduction of any toxic or infectious substances and be simple to perform without a sophisticated apparatus. The method that we describe satisfies all of these criteria.

SUMMARY OF THE INVENTION

According to a first aspect of the invention, the compounds of this invention are illustrated by Formula (I):

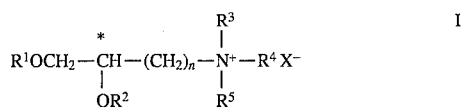

or an optical isomer thereof, wherein $R^1$ and $R^2$ are independently an alkyl, alkenyl, or alkynyl group of 6 to 24 carbon atoms; $R^3$, $R^4$ and $R^5$ are independently hydrogen, alkyl of 1 to 8 carbon atoms, aryl or aralkyl of 6 to 11 carbon atoms; alternatively two or three of $R^3$, $R^4$ and $R^5$ are combined with the positively charged nitrogen atom to form a cyclic structure having from 5 to 8 atoms, where, in addition to the positively charged nitrogen atom, the atoms in the structure are carbon atoms and can include one oxygen, nitrogen or sulfur atom; n is 1 to 8; and X is an anion.

According to other aspects of the invention, liposome and pharmaceutical formulations are claimed: said liposome formulations comprising up to 10% by weight of a biologically active substance, 1% to 20% by weight of a lipid component comprising a compound of Formula I in a quantity of from about 1% to 100% by weight, and an aqueous solution in a quantity sufficient to make 100% by volume; and said pharmaceutical formulations comprising a therapeutically effective amount of a drug, an optional pharmaceutically acceptable excipient, and a lipid component comprising a compound of Formula I in a quantity of from about 1% to 100% by weight.

According to another aspect of the invention, a polyanion-lipid complex, formed from a compound of Formula I and a polyanion, is claimed.

According to yet another aspect of the invention, a method is claimed for forming a polyanion-lipid complex, said method comprising the steps of contacting a liposomal composition prepared from a positively charged liposome-forming lipid with a negatively charged polyanion.

According to still another aspect of the invention, a positively-charged polynucleotide-liposome complex is claimed, comprising a lipid of Formula I and a polynucleotide.

According to a further aspect of the invention, a method is claimed for preparing a positively-charged polynucleotide-lipid complex. The method comprises the steps of contacting a positively charged liposome made from a lipid of Formula I with a polyanion.

According to yet another aspect of the invention, a method is claimed for introducing a polyanion into a cell. The method comprises forming a liposome from a lipid of Formula I, contacting the liposome with a polyanion to form a positively-charged polyanion-liposome complex, and incubating the complex with a cell.

According to still another aspect of the invention, a method is claimed for intracellularly delivering a biologically active substance, which method comprises forming a liposome comprising a lipid of Formula I and a biologically active substance, and incubating the liposome with a cell culture.

According to a further aspect of the invention, an antigenic formulation is claimed, comprising an antigen and a compound of Formula I.

According to a still further aspect of the invention, a method is claimed for the transdermal, topical or ocular delivery of a drug. The method comprises the steps of forming a liposome comprising a compound of Formula I and the drug; and applying the liposome to the skin or mucous membranes of a human or animal subject.

According to another aspect of the invention, double coated liposome complexes are claimed, comprising a polyanion, a lipid of Formula I, and a negatively charged co-lipid.

According to a still further aspect of the invention, a method is claimed for making said double-coated complexes, comprising forming a liposome from a lipid or Formula I; contacting it with a polyanion; and contacting the resulting complex with an excess of negatively-charged lipid.

DETAILED DESCRIPTION OF THE INVENTION

Figure 1A:
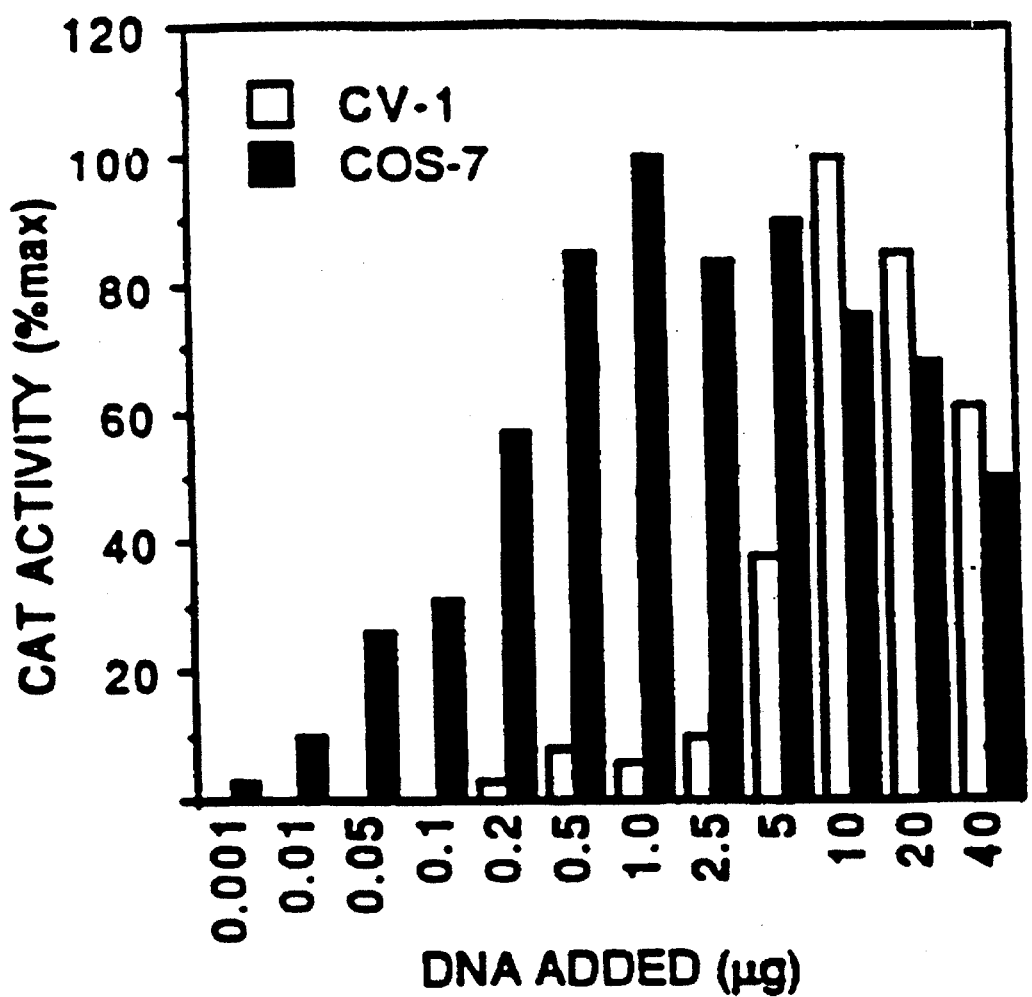
FIG. 1A is a bar graph of transfection efficiency as a function of DNA concentration.

Several advantages flow from the compounds and methods of the present invention. One of the advantages of the methods and materials disclosed herein is that they permit up to 100% entrapment of polyanionic substances by an exceedingly convenient and practical protocol. Another advantage of the liposome compositions disclosed herein is that they are not subject to instability due to leakage of the entrapped polyanionic substance. Still another advantage is that the convenient and practical methodology disclosed herein yields compositions of matter with unique properties enabling entry of the entrapped polyanionic substance, such as DNA, into living cells. This property of the resulting lipid/polyanion complex enables the expression of biological activities to extents not previously seen in these cells. And still further, this methodology leads to results that have not been obtained with conventional liposomes.

The positively charged pharmaceutical formulations, particularly liposomes, of this invention are pharmaceutically advantageous: the presentation of positively charged materials to the negatively charged cell surface results in better uptake of the pharmaceutical materials by the cells.

The unique advantages of the technology disclosed herein are of two types. First, the compounds of Formula I represent novel positively charged liposome forming lipids, which can be used for the formation of positively charged liposomes in which drugs or other materials can be encapsulated in the conventional manner. The uniqueness of this aspect of the invention depends on the chemical structure of the compounds of Formula I. The principal advantages of this structure derive from the geometry of the two parallel aliphatic chains, the overall positive charge of the molecule itself, and the chemical stability of the ether linkages. The geometry of the two aliphatic chains enables the organization by the compounds of Formula I into stable bilayer structures. These bilayers comprise the overall structure of the liposome itself. The positive charge on the molecules of Formula I provides the resulting liposome with an overall positive charge, resulting in a net positively charged liposome. The ether linkage of the aliphatic chains provides the chemical stability important for the type of chemical structure synthesized and for the type of applications described herein. Both hydrophobic and hydrophilic biologically active substances can be incorporated into the resulting liposomes using conventional liposome technology commonly known by those familiar with the art. The resulting liposomes produced are better than those produced with other commonly available materials, because the compounds of Formula I have a geometry more compatible with the formation of bilayers, leading to a liposome with greater physical stability.

Thus, compounds of Formula I do not suffer from the drawbacks of amines employed in liposomes before this invention. The ether linkage of the compounds of Formula I is highly stable in liposomes. Additionally, the compounds of Formula I are not leached out of nor do they otherwise migrate out of the liposome matrix as do steryl amines and other amines. Moreover, concerns of toxicity are significantly reduced with the compounds of Formula I. Still further, the parallel geometry of the aliphatic chains in the preferred embodiments of the compounds of Formula I overcomes problems with bilayer compatibility that are common to molecules such as dioctadecyldimethyl ammonium bromide.

The second unique advantage of the technology disclosed herein is derived from the novel method for incorporating polyanionic biologically active substances into a liposome complex. This complex is composed of positively charged liposomes prepared from compounds of Formula I or other positively charged lipids, and a polyanionic substance. According to the method, premade liposomes are contacted with the polyanionic substance in an aqueous environment. The precise nature of the complex formed is determined by the chemical composition of the positively charged liposomes used and by the molar ratio of total positive charges on the liposome, to the total negative charges on the polyanion. Precise tuning of these compositional aspects determines the biological activity of the final product produced. The advantages of this methodology over other liposome technology commonly known in the art are that the new method results in up to 100% entrapment of the biologically active substance, the entrapped material does not leak out in storage, and the complex has unique biological properties not shared by liposome encapsulated material prepared in the conventional manner. Furthermore, by utilizing double-coated complexes, preferential delivery to a specific site in the body can be obtained in vivo, to ultimately provided site-specific intracellular delivery via the positively-charged lipid complex portion of the double-coated complex.

A. DEFINITIONS

An aliphatic chain comprises the classes of alkyl, alkenyl and alkynyl defined below. A straight aliphatic chain is limited to unbranched carbon chain radicals.

Alkyl refers to a fully saturated branched or unbranched carbon chain radical having the number of carbon atoms specified, or up to 22 carbon atoms if no specification is made. For example, alkyl of 1 to 8 carbon atoms refers to radicals such as methyl, ethyl, propyl, butyl, pentyl, hexyl, heptyl, and octyl, and those radicals which are positional isomers of these radicals. Lower alkyl refers to alkyl of 1 to 4 carbon atoms, such as methyl, ethyl, n-propyl, isopropyl, n-butyl, isobutyl, secbutyl, and tert-butyl. Alkyl of 6 to 24 carbon atoms includes hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl.

Alkenyl refers to any branched or unbranched unsaturated carbon chain radical having the number of carbon atoms specified, or up to 22 carbon atoms if no limitation on the number of carbon atoms is specified; and having 1 or more double bonds in the radical. Alkenyl of 6 to 24 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical.

Alkynyl refers to hydrocarbon radicals of the scope of alkenyl, but having 1 or more triple bonds in the radical.

An antigen is any substance to which an organism can elicit an immune response.

Antisense refers to a nucleotide sequence that is complementary to a specific sequence of nucleotides in DNA or RNA.

Aryl refers to phenyl or naphthyl.

Aralkyl of 7 to 11 carbon atoms refers to a radical having an alkyl group to which is attached a benzene ring such as the benzyl radical, phenethyl, 3-phenylpropyl, or the like.

Biologically active substance refers to any molecule or mixture or complex of molecules that exerts a biological effect in vitro and/or in vivo, including pharmaceuticals, drugs, proteins, vitamins, steroids, polyanions, nucleosides, nucleotides, polynucleotides, etc.

Buffers referred to in this disclosure include "Tris," "Hepes", and "PBS." "Tris" is tris(hydroxymethyl)aminomethane, and for the purpose of the preferred embodiments of this invention is used at about pH 7. "Hepes" is N-2-hydroxyethylpiperazine-N'-2-ethanesulfonic acid, also used here as a buffer at about pH 7. Phosphate-buffered saline, or "PBS," is 10 mM sodium phosphate and 0.9 wt. % NaCl, used as an isotonic physiological buffer at pH 7.4.

A cell is any one of the minute protoplasmic masses which make up organized tissue, comprising a mass of protoplasm surrounded by a membrane including nucleated and unnucleated cells and organelles. An intact cell is a cell with an intact membrane that has not released its normal intracellular components such as enzymes, organelles, or genetic material. A viable cell is a living cell capable of carrying out its normal metabolic functions.

A complex (or a liposome complex) is defined as the product made by mixing pre-formed liposomes comprising a compound of Formula I with a polyanion (e.g., polynucleotide) or some other macromolecule containing multiple negative charges. Such a complex is characterized by an interaction between the polyanion and lipid components that results in the elution of the polyanion and liposome together as substantially one entity through a gel filtration column that separates on the basis of the Strokes' radius or by some other separation procedure.

A charge ratio refers to a quantitative relationship between the net positive charges contributed by the lipid and the net negative charges contributed by the polyanion in a complex. The charge ratio herein is expressed as positive to negative, i.e., 5:1 means five net positive charges on the lipid per net negative charge on the polyanion.

Double-coated complexes are prepared from liposome complexes bearing a net positive charge. Liposome complexes bearing a net positive charge are prepared as described in the preceding paragraph, using a greater molar amount of positively charged lipid than the molar amount of negative charge contributed by the polyanion. These positively charged complexes are mixed with negatively charged lipids to produce the double-coated complexes. If sufficient negatively-charged lipid is added, the final complex has a net negative charge. This definition includes liposomes that have further modifications on the surface, such as the incorporation of antibodies or antigens therein.

DOTMA is the most preferred lipid of Formula I, known as N-(2,3-di(9-(Z)-octadecenyloxy))-prop-1-yl-N,N,N-trimethylammonium chloride. DOTMA vesicles are liposomes made from DOTMA.

DNA represents deoxyribonucleic acid, which may optionally comprise unnatural nucleotides. DNA may be single stranded or double stranded.

Drug refers to any therapeutic or prophylactic agent other than a food which is used in the prevention, diagnosis, alleviation, treatment, or cure of disease in man or animal. (Therapeutically useful polynucleotides and polypeptides are within the scope of this definition for drugs).

Intracellularly means the area within the plasma membrane of a cell, including the cytoplasm and/or nucleus.

A lipid of Formula I is to be understood as the class of lipids set forth in the Summary of the Invention. Exemplary cyclic structures represented by two or three of $R^3$, $R^4$ and $R^5$ are quinuclidino, piperidino, pyrrolidino and morpholino.

A liposome formulation is a composition of matter including a liposome, which includes a material encapsulated in the liposome, for diagnostic, biological or therapeutic use.

A liposome-polyanion complex is a composition of matter produced by contacting a solution of polyanion with a preparation of cationic liposomes produced from a compound of Formula I (with optional co-lipids as appropriate).

Optional or optionally means that the subsequently described event or circumstance may or may not occur, and that the description includes instances where said event or circumstance occurs and instances in which it does not.

An optional co-lipid is to be understood as a structure capable of producing a stable liposome, alone, or in combination with other lipid components, and is preferably neutral, although it can alternatively be positively or negatively charged. Examples of optional co-lipids are phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylchloine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylchloine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids are, e.g., stearylamine, dodecylamine, hexadecylamine, acetyl palmitate, glycerol ricinoleate, hexadecyl stereate, isopropyl myristate, ampho-teric acrylic polymers, triethanolamine-lauryl sulfate, alkylaryl sulfate polyethyloxylated fatty acid amides, dioctadecyldimethyl ammonium bromide and the like.

A pharmaceutical formulation is a composition of matter including a drug, for therapeutic administration to a human or animal.

A pharmaceutical acceptable anion is an anion which itself is non-toxic or otherwise pharmaceutically acceptable and which does not render the compound pharmaceutically unacceptable. Examples of such anions are the halides anions, chloride, bromide, and iodide. Inorganic anions such as sulfate, phosphate, and nitrate may also be used. Organic anions may be derived from simple organic acids such as acetic acid, propionic acid, glycolic acid, pyruvic acid, oxalic acid, malic acid, malonic acid, succinic acid, maleic, acid, fumaric acid, tartaric acid, citric acid, benzoic acid, cinnamic acid, mandelic acid, methane sulfonic acid, ethane sulfonic acid, p-toluenesulfonic acid, and the like.

A polyanion is a biologically active polymeric structure such as a polypeptide or a polynucleotide, wherein more than one unit of the polymer bears a negative charge and the net charge of the polymer is negative.

A polynucleotide is DNA or RNA containing more than one nucleotide. Polynucleotides are intended to include ppp(adenyl 2'→5')$_n$ adenylate, n$\geq$ 2, represented by 2–5A. A polynucleotide comprising riboinosinic acid and ribocytidylic acid is called poly IC. Polynucleotides are those that can be made by chemical synthetic methodology known to one of ordinary skill in the art, or by the use of recombinant DNA technology, or by a combination of the two.

A polypeptide is a biologically active series of two or more amino acids coupled with a peptide linkage.

RNA represents ribonucleic acid which may optionally comprise unnatural nucleotides. RNA may be single stranded or double stranded.

A suitable aqueous medium for forming liposomes from the dried lipid film is to be understood as, for example, water, an aqueous buffer solution, or a tissue culture media. For example, a suitable buffer is phosphate buffered saline, i.e., 10 mM potassium phosphate having a pH of 7.4 in 0.9% NaCl solution. The pH of the medium should be in the range of from about 2 to about 12, but preferably about 5 to about 9, and most preferably about 7.

A suitable solvent for preparing a dried lipid film from the desired lipid components is to be understood as any solvent that can dissolve all of the components and then be conveniently removed by evaporation or lyophilization. Exemplary solvents are chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Mixtures of two or more solvents may be used in the practice of the invention.

A stable transfectant is a living cell into which DNA has been introduced and become integrated in the genomic DNA of that cell Topical administration includes application to any surface of the body, including ocular administration and administration to the surface of any body cavities.

Transdermal administration through the skin with a systemic effect.

Transfection refers for the purpose of this disclosure to the introduction of DNA or RNA into a living cell Unnatural nucleotides include those which are commercially available or which can be readily made by means known to those of ordinary skill in the art.

"Z" refers to the cis form of the aliphatic radicals in Formula I.

The compounds of these may be prepared as a racemic mixture of D,L-isomers or as the individual D or L isomer. Because of the availability of D or L starting materials, certain of these compounds are readily prepared as the individual isomer. However, unless the specific isomer is designated, it should be understood that this invention covers both the pure D or L- isomers as well as the D,L-racemate.

Compounds of Formula I have one asymmetric site, (marked above as *), and thus can exist as a pair of optical isomers. Individual isomers of compounds of Formula I are named herein using the IUPAC R-S convention, sometimes called the "sequence rule." A description of the R-S convention may be found, for example, in "Introduction to Organic Chemistry" by A. Streitwieser, Jr. and C. Heathcock, (Macmillan Pub. Co., New York, 1976), pages 110–114. Where appropriate, the optical activity of a compound may be indicated by (+) or a (−) for the individual isomers, or (±) for the racemic mixture, referring to the direction in which a solution of the compound rotates a plane of polarized light. For the purposes of the appended claims, it should be understood that racemic mixtures of the compounds of Formula (I) as well as either isomer taken alone are within the scope of this invention.

B. UTILITY

The compounds of Formula I are particularly useful in the preparation of liposomes, but may be used in any of the many uses for which cationic lipids find application. For example, they may be used in industrial applications, in food or feeds, in pharmaceutical formulations, cosmetological compositions, or other areas where lipids may be employed. These compounds may also be used in cosmetology, for example, in makeups, lipstick, eyeshadow material, fingernail polishes, body lotions, moisturizing creams, and the like. They may also be used for application to the hair, either alone or in combination with other materials, such as in shampoos, hair conditioners, permanent wave formulations or hair straighteners, or as components in hair creams, gels, and the like.

Of particular interest is the use of these compounds in pharmaceutical formulations, particularly topical formulations such as ointments, gels, pastes, creams, and the like; and more particularly for the preparation of pharmaceutical formulations containing liposomes. The consistency of the formulation depends on the amount of aqueous solution used to make the formulation. In such formulations containing compounds of this invention, drugs which are insoluble or only sparingly soluble themselves in aqueous solutions can be solubilized so that a greater concentration of drug can be presented to the body.

In pharmaceutical formulations, these compounds may be used in those contexts where cationic lipids are acceptable for the formulation of creams, pastes, gels, colloidal dispersions, and the like. For additional information, reference is made to *Remington's Pharmaceutical Society,* 17th Edition, Mark Publishing Company, Easton, Pa. (1985), or any other standard treatise on pharmaceutical formulations.

Other aspects of this invention are directed to the finding that formulations comprising the compounds of Formula I are useful for achieving desirable intracellular delivery of specific biologically active substances, such as nucleosides, nucleotides, oligoand poly-nucleotides, steroids, peptides and proteins, and other appropriate natural or synthetic molecules or macromolecules. The intracellular delivery can be into the cytoplasm, into the nucleus, or both. Such intracellular delivery can be achieved in tissue culture and may be used as an aid in transfecting cells with desired polynucleotide sequences (e.g., deoxyribonucleic acid, DNA) to aid in cloning of specific sequences. Thus, formulations comprising: (1) compounds of Formula I, and (2) DNA or complementary DNA (cDNA)—in appropriate plasmids containing promoters, enhancers and the like as desired—, can be utilized to achieve transfection of cells and to obtain stable transfectants as part of the process of cloning (via recombinant DNA technology well known to those familiar in the art) various desired sequences to yield the corresponding expressed products (e.g., proteins and peptides). The technology of utilizing a compound of Formula I or other positively-charged lipid formulation to achieve efficient transfection and to obtain stable transfectants with the desired DNA sequences can enhance the ability to achieve the desired end result of the cloning procedure. This technology provides a less toxic and more efficient route for the delivery of polynucleotides to cells than other presently-used techniques such as calcium phosphate precipitation.

Intracellular delivery can also be achieved in the whole organism and may be useful in several diverse applications. For example, enzyme-replacement therapy can be effected by direct intracellular introduction of the desired enzymes, or by appropriate transfection of cells with a DNA sequence encoding the desired protein, with the appropriate promoters and the like include so as to give sufficient gene expression. If desired, inducible promoters can be employed to allow control in turning on or turning off the gene of interest. Other applications of intracellular delivery that can be achieved employing the compounds of Formula I or other positively-charged lipid formulations for transfection of DNA include but are not limited to hormone replacement therapy (e.g., insulin, growth hormone, etc.), blood coagulation factor replacement therapy, replacement therapy for other blood disorders such as β-thalassemia or other hemoglobin deficiencies, adenosine deaminase deficiency, neurotransmitter replacement therapy, and the like. Another application utilizing such formulations to enhance intracellular delivery includes the delivery of "antisense" RNA oligomers to selectively turn off expression of certain proteins. Compounds of this invention can also be used to deliver biologically active materials across the blood brain barrier.

Formulations comprising the compounds of Formula I can also be used to transfect and transform cells in vitro to introduce a desired trait before implantation of the transformed cells into the whole organism. An example of this application is to transfect bone marrow cells with a desired gene, such as one coding for normal adult hemoglobin sequences to correct the deficiency in patients with disorders such as β-thalassemia, adenosine deaminase deficiency, and sickle-cell anemia. The bone marrow cells can be transfected in vitro, and then the appropriately transfected cells can be transfused into the marrow of the patient. Alternatively, the cells can be transfected in vivo as described herein. Procedures such as calcium phosphate precipitation are much less efficient in effecting such transfections, making them unsuitable for practical use. Other means of achieving transfection that have been applied in vitro include the use of viral vectors (such as SV-40 and retroviruses). However, these viruses are oncogenic and thus cannot be safely used for transfecting cells in vivo or in vitro for ultimate transfusion in vivo.

Intracellular delivery utilizing formulations of compounds of Formula I is also useful for delivery of antiviral compounds (such as protease inhibitors, nucleoside derivatives, nucleotides, or polynucleotides such as 2–5A); anticancer compounds (including but not limited to nucleosides/ nucleotides such as 5-fluorouracil, adenosine analogs, cytosine analogs, and purine analogs); antibiotics such as anthracyclines (for example adriamycin and daunomycin) and bleomycin; protein antibiotics such as nuocarzinostatin, marcomomycin, and auromomycin; alkylating agents such as chlorambucil, cyclophosphamide, nitrosoureas, melphalan, aziridines, alkyl alkanesulfonates; platinum coorindation compounds; folate analogs such as methotrexate; radiation sensitizers; alkaloids such as vincristine and vinblastine; cytoskeleton-disrupting agents; differentiating agents; and other anticancer agents. This aspect of the invention can be particularly useful in overcoming drug resistance such as caused by reduced uptake mechanisms of the drug by the cells.

Further selectivity can be achieved by incorporating specific molecules such as antibodies, lectins, peptides or proteins, carbohydrates, glycoproteins, and the like, on the surface of the liposome vesicles, which can then serve to "target" the drugs formulated with the compounds of Formula I to desired tissues bearing appropriate receptors or binding sites for the ligand attached to the vesicle surface. Further selectivity can also be achieved by coating the liposome vesicles with a neutral or negatively-charged optional co-lipid (to eliminate non-specific adsorption to cells) before addition of the targeting ligand as described above.

The use of formulations comprising compounds of Formula I or other positively-charged lipid formulations of polynucleotides (including DNA and RNA) for intracellular delivery is superior than other available methodology, such as calcium phosphate coprecipitation, or polylysine or DEAE-dextran complexation of polynucleotides, as the formulations of this invention are much less toxic and deleterious to the living cells than are the other above mentioned procedures. Furthermore, the formulations using compounds of Formula I are much more efficient in transfecting cells. Additionally, the use of liposomes made from the compounds of Formula I to effect intracellular delivery of the liposome contents is superior to the use of polyethyleneglycol (PEG) or glycerol-induced fusion of ordinary neutral or negatively-charged vesicles to cells, because the vesicles of the compounds of Formula I do not require the use of the PEG or glycerol as fusion-inducing agents. These agents are highly deleterious to the viability and integrity of cells.

Another method that has been employed to induce fusion of liposomes with cells involves incorporation of viral fusion proteins (such as the fusion protein from Sendai virus) on the liposome surface. However, such techniques are not only tedious but they also can result in formation of antibodies by the animal against the viral proteins, thus severely limiting the utility of this approach.

Other applications of the formulations of this invention comprising the compounds of Formula I relates to localized delivery of drugs through the stratum corneum, and to transdermal delivery of drugs. Liposome vesicles comprising the compounds of Formula I can serve to introduce certain compounds into and through the stratum corneum. Depending on the degree of penetration enhancement (which is also influenced by the drug and the incorporation of other components in the liposome, such as phospholipid bilayer perturbing agents such as phosphatidylethanolamine, Azone®, and lysolecithin), the formulations can serve to enhance a localized effect of the drug. This enhancement would be applicable to the treatment of a localized outbreak of herpes simplex virus type 1 or 2 with an interferon or an interferon inducer, and/or with a nucleoside such as an acyclic guanosine nucleoside analog such as acyclovir or 9-(1,3-dihydroxy-2-propoxymethyl)guanine, or 9-(1,3-dihydroxy-2-propoxymethyl) guanine dipalmitate. In other cases, the liposomes comprising compounds of Formula I can serve to enhance systemic uptake of the drug by transdermal absorption, for example as with topical applicationjs of Synalar® in DOTMA formulations.

Another application of certain formulations comprising the compounds of Formula I is the enhancement of a specific immune response, such as humoral and/or cellular immunity, to an antigen of interest which is incorporated in the lipid-containing vesicles. Thus, such preparations can serve as specific adjuvants for vaccines (including viral, bacterial, rickettsial, parasitic, and cancer vaccines), antigen preparations, as well as other proteins or peptides including synthetic peptides of interest. Additional components may be included to further enhance the immune response, e.g., immunostimulants such as muramyl dipeptide/analogs. N-acetylmuramyl-L-threonyl-D-isoglutamine may be particularly useful here.

C. DOSAGE AND ADMINISTRATION

Administration of the active compounds and salts described herein can be via any of the accepted modes of administration for the biologically active substances that are desired to be administered. These methods include oral, topical, parenteral, ocular, transdermal, nasal, and other systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

Topical formulations composed of compounds of Formula I, other lipid material, other penetration enhancers, phosphatidylethanolamine and biologically active drugs or medicaments can be applied in many ways. The solution can be applied dropwise, from a suitable delivery device, to the appropriate area of skin or diseased skin or mucous membranes and rubbed in by hand or simply allowed to air dry. A suitable gelling agent can be added to the solution and the preparation can be applied to the appropriate area and rubbed in. Alternatively, the solution formulation can be placed into a spray device and be delivered as a spray. This type of drug delivery device is particularly well suited for application to large areas of skin, to highly sensitive skin or to the nasal or oral cavities.

For oral administration, a pharmaceutically acceptable non-toxic composition is formed by the incorporation or any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. The exact composition of these formulations may vary widely depending on the particular properties of the drug in question. However, they will generally comprise from 0.01% to 95%, and preferably from 0.05% to 10%, active ingredient for highly potent drugs, and from 40–85% for moderately active drugs.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

The amount of active compound administered will of course, be dependent on the subject being treated, the type and severity of the affliction, the manner of administration and the judgment of the prescribing physician. In addition, if the dosage form is intended to give a sustained release effect, the total dose given will be integrated over the total time period of the sustained release device in order to compute the appropriate dose required. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 30% (w/v) of the total formulation. The drug component of the formulation will most likely be less than 20% (w/v) of the formulation and generally greater than 0.1% (w/v).

In general, topical formulations using a compound of Formula I are prepared in gels, creams or solutions having an active ingredient in the range of from 0.001% to 10% (w/v), preferably 0.01 to 5%, and most preferably about 1% to about 5%. (Of course, these ranges are subject to variation depending upon the potency of the drug, and could in appropriate circumstances fall within a range as broad as from 0.0001% to 20%.) These guidelines would pertain, for example, to topically applied transglutaminase inhibitors such as 5-(N-benzyloxycarbonyl-L-paratyrosinamidomethyl)-3-chloro- 4,5-dihydroisoxazole, also named in its preferred form as (S,S)-2-1(1-benzyloxymethanamido)-N-[(3-chloro-4,5-dihydroisoxazol- 5-yl)methyl]-3-(4-hydroxyphenyl)-propanamide, which could be applied twice daily in a formulation containing 2.5% active ingredient. Similarly, for Butoconazole nitrate (see Example 4, Part 4), the preferred amount of active ingredient will be about 1%. Another example of a topical formulation is the class of 5-lipoxygenase antipsoriatic agents, such as lonapalene, which is preferably formulated with about 1% active ingredient. In all of these exemplary formulations, as will other topical formulations, the total dose given will depend upon the size of the affected area of the skin and the number of doses per day. The formulations can be applied as often as necessary, but preferably not more than about 3 times per day.

Other topical formulations including a compound of Formula I also fall within these guidelines. The acyclic guanosine nucleoside analog, acyclovir, or 9-(1,3-dihydroxy-2-propoxy methyl)guanine dipalmitate (also known as DHPG dipalmitate), is topically applied in formulations using most preferably about 3% (w/w) active ingredient. Likewise, a topical formulation of ketorolac, i.e., 5-benzoyl-1,2-dihydro-3H-pyrrolo[1,2-a]pyrrole-1-carboxylic acid, can be used having about 3% active ingredient; or about 0.5% active ingredient, as a salt, for ocular administration. Interferon ($\alpha$-, $\beta$ or $\gamma$-interferons, or a mixture of any of these), is used at 100 to $10^9$ units per gram of cream, gel, lotion, ointment or liposome formulation containing a compound of Formula I, more preferably from $10^4$ to $10^8$ units per gram, and most preferably from $10^5$ to $10^7$ units per gram. The acyclic nucleoside analog may be used alone or in combination with any or all of the interferons. The gel, cream, ointment, lotion, or liposome formulation-containing the nucleoside and/or interferon is applied topically or intravaginally to the area of the viral outbreak, and can be applied 1 to 6 times daily, preferably 1 to 4 times daily, for as many days as needed, typically from 2 to 8 days.

The oral DHPG dipalmitate, or an analog thereof, can be formulated using a compound of Formula I, as a solution, tablet or capsule, and be administered as a dose of about 500 mg active ingredient per day per 70 kg person. Doses can be given up to several times daily, but are more typically given 3 to 5 times over a period of a week.

The systemic DHPG dipalmitate, or an analog thereof, can be formulated, using a compound of Formula I, as a solution and administered at a dose of about 350 mg per day per 70 kg person. Doses can be given daily, but are more generally given 3 to 5 times per week and after the first week the patient's condition is evaluated.

For the inotropic agent, N-cyclohexyl-N-methyl-4-( 2-oxo-1,2,3,5-tetrahydroimidazo-[2,1-b]quinazolin-7-yl)-oxybutyramide, formulated with a compound of Formula I, an appropriate dosage range for oral or intravenous administration would be from about 0.1 to about 25 mg/kg, and preferably from about 1 to about 10 mg/kg.

Prostaglandin analog formulations using a compound of the Formula I are generally administered in the range of about 1 mg of active ingredient per 70 kg person.

For suitable nicardipine dosage and administration, the full disclosure of U.S. Ser. No. 06/877,812, filed Jun. 24, 1986, is hereby incorporated by reference.

Regarding vaccine administration, to achieve the desired immune response, the antigen in the formulation comprising a compound of Formula I is administered to an animal or mammal in need thereof, either by injection (such as subcutaneous, intraperitoneal, intramuscular or intravenous) or orally, or by intranasal administration. The formulation of a vaccine using the compounds of Formula I described herein will employ an effective amount of antigenic material. That is, there will be included an amount of antigen which, in combination with the adjuvants, will cause the subject to produce a specific and sufficient immunological response so as to impact protection to the subject from the subsequent exposure to the material or organism against which the vaccine is intended to be effective. Alternatively, the antibody will combine with a hormone or naturally occurring material in such a way as to alter biological processes such as growth.

No single dose designation can be assigned which will provide specific guidance for each and every antigen which may be employed in this invention. The effective amount of antigen will obviously be a product of its inherent activity and molecular weight, and will be a function of the degree to which the specific antigen can be purified from its source. It is contemplated that the lipid or liposome formulations of this invention may be used in conjunction with whole cell or virus vaccines as well as purified antigens or subunit or peptide vaccines prepared by recombinant DNA techniques or synthesis.

However, as a general matter, the amount of antigen used can range from 0.01 µg/kg to 1 mg/kg, and more preferably from 0.1 to 200 µg/kg. A primary vaccination is administered, and if desired this can be followed by one or more booster vaccinations given usually from 2 weeks to several months after the primary vaccination. If, desired, booster vaccinations can be administered at regular intervals (such as on a yearly schedule or a schedule of every two to three years.). The antigens or herpes viruses, influenza viruses, malaria parasites, hepatitis viruses (such as hepatitis B surface or pre-S antigens), or retroviruses such as human immunodeficiency viruses, may be particularly useful for preparing vaccines of this invention. If N-acetylmuramyl-L-threonyl-D-isoglutamine is included to further enhance the response, the dose of this component can range from 0.001 to 1 mg/kg, and more preferably from 0.01 to 0.5 mg/kg.

D. SPECIFICALLY PREFERRED EMBODIMENTS

1. Lipids, Liposomes, and Pharmaceutical Formulations

The preferred compounds of Formula I are those wherein $R^1$ and $R^2$ are approximately the same length and are independently alkyl or alkenyl of 10 to 20 carbon atoms; $R^3$, $R^4$, and $R^5$ are methyl or ethyl; n is 1 to 4; and X is a halide ion. In the more preferred group, n is 1, and $R^1$ and $R^2$ are the same length.

The following racemic compounds and the optical isomers thereof are examples of preferred compounds:

N-(2,3-di-(9-(Z)-octadecenyloxy))-prop-1-yl-N,N,N-trimethylammonium chloride (DOTMA, the most preferred compound);

N-(2,3-di-octadecyloxy)-prop-1-yl-N,N,N-trimethylammonium chloride;

N-(2,3-di-(4-(Z)-decenyloxy))-prop-1-yl-N,N,N-trimethylammonium chloride;

N-(2,3-di-hexadecyloxy)-prop-1-yl-N,N,N-trimethylammonium chloride ("BISHOP");

N-(2,3-di-decyloxy)-prop-1-yl-N,N,N-trimethylammonium chloride;

N-(2-hexadecyloxy-3-decyloxy)-prop-1-yl-N,N,N-trimethylammonium chloride;

N-(2-hexadecyloxy-3-decyloxy)-prop-1-yl-N,N-dimethylamine hydrochloride;

N-(9,10-di-decyloxy)-dec-1-yl-N,N,N-trimethylammonium chloride;

N-(5,6-di-(9-(Z)-octadecenyloxy))-hex-1-yl-N,N,N-trimethylammonium chloride; and N-(3,4-di-(9-(Z)-octadecenyloxy))-but-1-yl-N,N,N-trimethylammonium chloride.

Certain aspects of this relate to the use of liposomes made from the most preferred compound of Formula I, which liposomes are referred to herein as "DOTMA vesicles." DOTMA vesicles can be made with pure DOTMA, or with DOTMA in combination with other compounds of Formula I or other classes of positively charged lipids, for example similar to those of Formula I but containing ester instead of ether linkages on $R^1$ and/or $R^2$. Also, optional co-lipids can be combined with compounds of Formula I, such as DOPC and DOPE and the like. Optional co-lipids, such as DOPC and DOPE, can be mixed with the DOTMA analog in quantities equal to from 0 to 99%, more preferably from 10 to 90% and most preferably from 30 to 70%.

A list of optional co-lipids which can be used includes, for example, ternary or complex lipids, glycerides, cerides, etholides and sterides; i.e., any of several compounds having a hydrophilic and a lipophilic group, wherein the hydrophilic group is a phosphate, carboxylate, sulfate, amino, hydroxyl or choline group; and the lipophilic group is an alkyl or alkenyl, polyoxyalkylene or aromatic or cyclalkyl-substituted alkyl group. Polyethyleneoxy or glycol groups may be used. Additional lipids suitable for incorporation into these formulations can be found in the *McCutcheon's Detergents and Emulsifiers* and *McCutcheon's Functional Materials*, Allured Pub. Co., Ridgewood, N.J., U.S.A.

Preferred optional co-lipids are phospholipidrelated materials such as, for example, lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetyl phosphate, phosphatidylcholine and dipalmitoylphosphatidylcholine. Additional, non-phosphorus-containing lipids are, for instance, cetyl palmitate, glyceryl ricinoleate, hexadecyl stearate, isopropyl myristate, amphoteric acrylic polymers, triethanolamine-lauryl sulfate, alkanoyl-aryl sulfonates, and the like.

Additional additives may be long chain alcohols and diols; sterols, for example, cholesterol; phosphoric esters of fatty alcohols, for example, sodium dicetyl phosphate; alkyl-sulfates, for example, sodium cetyl sulfate; certain polymers such as polypeptides; positively-charged lipids such as stearylamine or dioctadecyldimethyl ammonium bromide; and proteins.

Typically, the aqueous liposome formulations of this invention will comprise 0.01 to 10% drug by weight (i.e., 10% is 100 mg drug per ml), 1 to 20% lipid by weight comprising a compound of Formula I in a quantity of 1 to 100% of this lipid component by weight, and an aqueous solution, that is, water which may or may not contain salts and buffers, in a quantity sufficient to make 100% by volume. Particularly preferred are formulations which comprise 0.1 to 5% drug and a lipid component comprising a compound of Formula I in a quantity of 50% or more by weight of the lipid component. Most preferred is a formulation comprising 1 to 5% drug by weight; up to 20% by weight of a lipid component, in turn comprising 10 to 100% by weight of a compound of Formula I; and an amount of aqueous solution sufficient (q.s.) to make 100% by volume.

Formulations of this invention, particularly liposomes, made with the compounds of Formula I will exhibit the properties of a positively charged entity when compounds of Formula I, comprising 1% or more by weight of the total weight, are used with a neutral liposome-forming material. Thus, other excipients, optional co-lipids and the like which are used for making liposomes, can be used in these formulations. One may use any combination of optional co-lipids with the compounds of Formula I so long as there is 1% or more of a compound of Formula I present in the formulation.

2. Liposome-Polyanion Complexes

Although the charge ratio is an important factor to consider in the preparation of DNA/DOTMA or RNA/DOTMA liposome complexes, it can vary considerably, depending upon the application. The charge ratio must be greater than 1:1, but is preferably in the range of 1000:1 to 1:1; more preferably 20:1 to 1:1; and most preferably 5:1 to 2:1.

The most appropriate ratio can routinely be determined by one of ordinary skill in the art. The precise ratio necessary for the best results must, however be optimized for each individual example. More specifically, the number of moles of anion in a stock solution of anion and the number of moles of cation in the stock liposome solution must first be quantitatively determined. When the ratio of cation of anion ranges between 0.5:1 and 2:1, significant turbidity generally develops upon mixing. (Significant turbidity is a net turbidity greater than the combined optical density of either component taken alone. The optical density is usually measured at 400 nm, but this wavelength is not critical.) This turbidity is a direct indication of complex formation between the cationic liposomes and the polyanionic substance. When the charge ratio of the added components is higher than 2 or lower than 0.5, complex formation still occurs, but it is not as readily apparent from gross changes in light scattering.

Having determined by light scattering that complex formation occurs between the polyanion and the positively charged liposome, it is then necessary to determine the ratio of the two components that yields the optimum biological effect. This is a simple, routine determination to one of ordinary skill in the art. The appropriate starting point would be at the ratio of greatest turbidity. For example, with respect to DNA transfection, it is necessary to determine the ratio of the two added components which leads to optimum expression of the transfected DNA. Specifically, with respect to DNA transfection of mouse L cells with a pSV2CAT plasmid, it is determined that while optimum light scattering occurrs at a ratio of about 1 to 1, the optimum ratio for transfection occurs at a charge ratio of about 2.5:1.

Polynucleotide/lipid complexes prepared as described are extremely convenient and useful for the delivery and expression of DNA and RNA in tissue culture cells. Similar complexes can be formed with non-polynucleotide materials for intracellular delivery, if they intrinsically contain or are otherwise provided with a negative charge. (E.g., ionic molecules can frequently acquire a negative charge by raising the pH; and a negative charge can also be added to a molecule by the covalent attachment of polyvalent negatively charged material such as polynucleotide, or sulfated polydextran.)

3. Double Coated Complexes

The complexes described hereinabove involve the addition of an excess of positively charged lipid material to a polyanion. The complex so produced bears a net positive charge enabling it to spontaneously intereact with negatively charged surfaces, such as the surface of tissue culture cells. Since most biologically interesting surfaces are negatively charged, this general approach is broadly applicable for inducing negatively charged materials to intereact with such negatively charged biological surfaces.

According to another aspect of the invention, it has been found useful to prepare complexes which do not interact spontaneously with the first negatively charged surface with which they come in contact. In order to achieve this result, "double coated" complexes are prepared by contacting the (positively charged) polyanion-lipid complexes with a second population of negatively charged liposomes. The quantity of negatively charged lipid added in this population exceeds the quantity of positive charged contributed by the initial population of lipid, so that the net charge on the resulting complexes is negative. The resulting double-coated complexes do not spontaneously intereact with tissue culture cells.

This methodology has several advantages over conventional liposome entrapment methods: 1) a relatively high capturing efficiency (up to 100%) can be obtained by this procedure, compared with other procedures for encapsulation of large polyanions that can achieve as little as 1% entrapment of less; 2) it is simple to manufacture the double-coated complexes from premade stable stocks; and 3) prior complexation with positive lipids gives unique physical properties to the initial polyanion of interest that can favorably effect its biological activity.

In addition, this procedure affords convenient preparation of complexes that associate with cells in a receptor-specific manner (See Example 10). This is accomplished by including a coupling reagent in the negatively charge liposome population. Antibodies, lectins, ligands and the like can be attached to the double-coated complexes in order to target them to a specific receptor.

With respect to the preparation of double coated complexes, some negatively charged liposomes are first prepared. These vesicles must contain at least one negatively charged lipid component, such as DOPG, in amounts equal from 1 to 100 mole %, preferably 10 to 90%, and most preferably 30 to 70%. A suitable lipid coupling agent, such as maleimide-PE, can be included in this formulation, depending on whether an additional covalently coupled surface component is desired in the final formulation. Maleimide-PE can be added at a mole percent from 0.01 to 20%, preferably 0.1 to 5%. A procedure for producing this type of covalent modification is given in the Examples. After preparation of the DNA/DOTMA liposome complexes according to the previous subsection, an aliquot of the negatively charged vesicles is added to produced the double coated vesicles. The molar ratio of DOTMA to the negatively charged lipid in the DNA/DOTMA liposome complex can vary considerably depending upon the desired charge of the final double-coated complex.

4. Transfection of Cells with Liposome Complexes

DNA-liposome complexes can be mixed with cells, either attached to a solid support or free floating in a suspension, under various conditions to achieve efficient transfection of the DNA. Cells can be grown on a solid support to a density of 100 to 1,000,000 cells per $cm^2$, but preferably 1000 to 100,000 cells per $cm^2$, most preferably about 30,000 cells per $cm^2$, using any conventional growth media or other conditions required to maintain viable cells. Cells in suspension culture can be used at a concentration of from about 100 to about $5 \times 10^7$ cells per ml, preferably from about $10^5$ to about $10^7$ cells per ml, and most preferably about $10^6$ cells per ml. The buffer to which the cells are exposed during the addition of DNA-liposome complex can vary, however, this buffer must be nearly isotonic. The tonicifier can be salts or sugars or other agents that are compatible with cellular viability in tissue culture. The buffer can contain any other components necessary for viability of the cells, but preferably the buffer is free of interfering serum or other protein components during an initial incubation phase which can last from about 5 minutes to 48 hours, but preferably 1 to 24 hours. The incubation can proceed at various temperatures including 0° to 55°, but preferably 15° to 42° and most preferably 20° to 38°. After this initial incubation with DNA-liposomes complex the cells can either be washed or not and the other components necessary for long term viability can be added back. The cells can be allowed to grow for an additional period of time if desired. The amount of DNA added to the cells in the form of a DNA-liposome complex can vary from between 0.001 and 10000 μg per 1,000,000 cells, but is preferably in the range of 0.01 to 1000 μg/1,000,000 cells, and most preferably 0.1 to 100 μg/1,000,000 cells.

This DNA transfection method can be used as part of a therapeutic protocol to treat genetic disorders. The treatment can be performed by either withdrawing cells from the affected patient, transfecting in vitro with the appropriate gene and reinjecting the successfully transfected cells; or by systemically administering the appropriate DNA directly into the affected patient with a suitable vehicle that will allow the transfection event to occur in vivo. The in vitro protocol is performed in the following way adapted from the literature (Anderson W. F., Science 226, 401–409 (1984); Williams D. A., Orkin S. H., Mulligan R. C., Proc. Nat. Acad. Sci. 83, 2655–2570 (1986)). A suitable quantity of tissue cells (from 10 million to 10 billion) is extracted from the patient. The tissue cells can be derived from various organs such as liver, spleen, blood or skin but most probably form bone marrow. The cells are prepared for tissue culture by trypsinization of the tissue or other means if necessary, grown in an appropriate media for a suitable length of time (e.g., 1 day to 2 weeks) and then transfected by adding the DNA/DOTMA liposome complex that is appropriate for the particular genetic disorder treated and with a composition consistent with the method described in the preceding paragraphs. The cells are incubated for a suitable length of time, approximately 4 to 72 hours, and the successfully transfected cells are washed and reinjected back into the affected individual. The affected individual can be treated with a high dose of radiation or by some chemical means prior to injection of the transfected bone marrow cells, in order to kill resident bone marrow cells. This gives the newly transfected cells a selective advantage as they repopulate the bone marrow. However, this last step may not be necessary, particularly if a selective advantage is built into the transfected polynucleotide.

The in vivo transfection protocol can be done in the following manner, adapted from Nicolau et al., Proc. Nat. Acad. Sci. 80, 1068–1072 (1983). DNA/DOTMA liposome complexes, or double coated DNA complexes, or covalently modified double coated complexes are prepared as previously described. The covalently modified complexes may contain attached antibodies, proteins, hormones, carbohydrates or other chemical modifications so as to target them to the particular cells of interest. For instance, the complexes can contain an antibody to endothelial cells in order to target the complexes to the endothelial cells; or they can contain antibody to a particular subpopulation of bone marrow cells in order to target the complexes to those cells. The administration to the affected individual can be intravenous (IV), subcutaneous (SC), intraperitoneal (IP), intramuscular (IM), topical, or by aerosol to the nose or lung. The therapeutic protocol can involve either a single treatment or the complex can be given as often as required. The IV dose can be given as a bolus or by slow infusion.

REACTION SCHEMES AND PREPARATION METHODS

Except where indicated, the substituents in each reaction scheme are commensurate in scope with the broadest claim.

REACTION SCHEME I

This reaction scheme is applicable to the synthesis of the compounds of Formula (I) in racemic or either optically active form. It is applicable when n is 1; $R^3$, $R^4$ and $R^5$ are the same or different and $R^5$ is not aryl; where $R^1$ and $R^2$ are the same; and where $X_a^-$ and $X_b^-$ are different anions.

The p-toluenesulfonate ester of formula (1) is commercially available in racemic and both optically active forms. In some cases, the 3-(dialkylamino)-1,2-propane diols of formula (3) are commercially available in racemic form.

To effect the formation of compounds of formula (2), the p-toluenesulfonate ester of formula (1) is allowed to react with an excess of an appropriate secondary amine in the absence of a solvent. This mixture is heated between about 25° and about 150° C., more preferably 75° C. for approximately 1 to about 5 days, preferably about 2 days. The amine is added in an excess molar amount, preferably about 2 to about 10 times the amount of the p-toluenesulfonate ester of formula (1) being used, more preferably about 5 times that amount.

The diol of formula (3) is then prepared by removal of the isopropylidene group from the amine of formula (2) in acidic methanol of pH between about 1 to about 5, preferably about pH 3. This mixture is heated between about 25° and about 65° C., preferably about 65° C., for about 1 to about 5 hours, preferably about 2 hours.

To effect the formation of the compound of formula (4), the diol is dissolved in an appropriate high boiling solvent such as xylene, mesitylene or the like. To this is added an alkali base, such as potassium tert-butoxide and an alkylating agent of the desired chain length and degree of unsaturation. For example the p-toluenesulfonate ester of oleyl alcohol can be used to effect the addition of 9-Z-octadecenyl groups. This mixture is then heated, preferably between about 100° and about 200° C., more preferably to about 140° C., with stirring for approximately 1 to about 5 hours, preferably about 3 hours. The base is added in an excess molar amount, preferably about 2 to about 4 times the amount of diol being used, more preferably about 3 times that amount. The alkylating agent is also added in an excess molar amount, preferably about 2 to about 4 times the amount of diol being used, more preferably about 3 times that amount.

The quaternary ammonium compound of Formula I is then prepared by condensing an alkyl chloride into a reaction vessel containing the compound of formula (4), after which the reaction vessel is sealed and heated to between about 50° and about 100° C., preferably about 70° C., for up to 60 hours. This procedure affords the tetraalkylammonium chloride product of Formula (I).

Alternatively, one quaternary ammonium compound of Formula I can be converted to another compound of For-

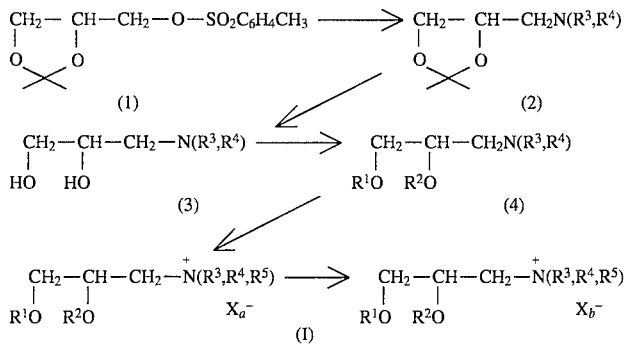

ammonium compound of Formula (I). This process is exemplified by Reaction Scheme II:

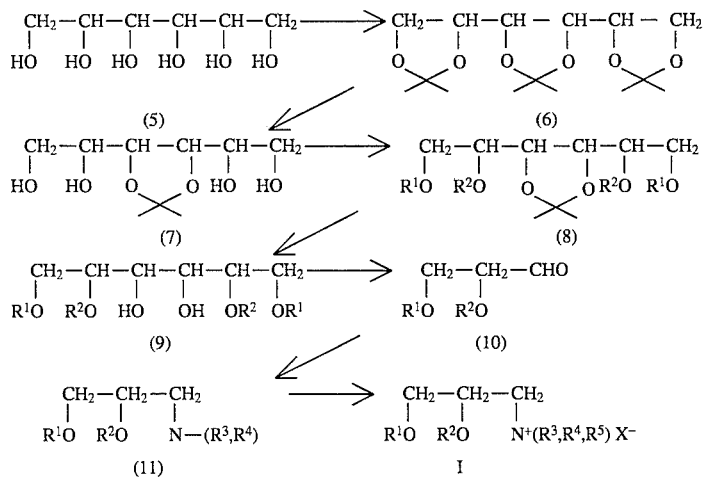

prepared by the alkylation of the compound of formula (4) with a dialkylsulfate in an appropriate solvent at or above room temperature. Depending on the reactivity of the dialkylsulfate, this mixture can be heated to 150° C. to obtain the product of Formula I. However, with a reactive dialkyl sulfate, room temperature is preferred. The alkylating agent is added in an excess molar amount, preferably between 1 and about 3 times the amount of compound of formula (4), more preferably 2 times that amount.

The quaternary ammonium sulfate of Formula I obtained in this manner can be converted to a quaternary ammonium chloride of Formula I by anion exchange. A solution of the sulfate form of a compound of Formula I in an appropriate organic solvent is treated with an excess molar amount of sodium chloride as a saturated solution in water. The two phases are mixed vigorously and allowed to separate. The organic layer is removed and the tetraalkylammonium chloride product of Formula I is isolated. The sodium chloride is used in an excess molar amount, preferably 1 to 10 times the amount of the sulfate compound of Formula I, more preferably about 5 times that amount.

This two-step procedure can be carried out at atmospheric pressure, avoiding the high pressures which can be generated in the preceding case.

REACTION SCHEME II

Alternatively, optically active compounds of Formula (I) commensurate in scope with Reaction Scheme I, can be prepared in the (S) absolute configuration by this Reaction Scheme II. Where n is 1, the compounds most analogous to glycerol, the compounds of this invention can be derived from D-mannitol. The two central hydroxy groups of mannitol are first protected by formation of a ketal, for example by formation of the acetonide of formula (7). The four remaining hydroxy groups are then converted to ethers of formula (8) using the appropriate long chain alkylating agent. The compound of formula (8) is hydrolyzed to that of formula (9), which is then chemically split into two units of aldehyde of formula (10) of 3 carbon atoms each, wherein two carbon atoms are substituted with a long chain alkyl, alkenyl or alkynyl group. The aldehyde functionality is then converted to a tertiary amine of formula (11) and then further converted to either the acid addition salt or a quaternary The D-mannitol-3,4-acetonide of formula (7) is prepared in two steps from commercially available D-mannitol (formula (5)). To effect this transformation, D-mannitol is allowed to react with 2,2-dimethoxypropane in acetone in the presence of an acid catalyst. This produces the D-mannitol-1,2:3,4:5,6-trisacetonide of formula (6), which is partially hydrolyzed in aqueous acetic acid to the D-mannitol-3,4-acetonide of formula (7).

To effect formation of compound (8), the acetonide (formula (7)) is dissolved in an appropriate polar solvent such as dimethylformamide, diethylformamide, or the like. To this is added a strong base, such as sodium hydride, at room temperature. This mixture is then heated, preferably between about 30° and about 100° C., more preferably to about 50° C., with stirring for approximately 30 to about 90 minutes, preferably about 60 minutes. To this is then added an alkylating agent of the desired chain length exemplified by the toluenesulfonate ester of oleyl alcohol or by 1-bromohexadecane. Following addition of the alkylating agent, the temperature is increased to between about 50° and about 150° C., preferably about 90° C., with additional stirring over a period of up to 2 hours, preferably about 1 hour. In the first addition, the base is added in an equal molar amount to the amount of acetonide being used and the alkylating agent is added in an equal molar amount. This sequence of adding a molar amount of base with heating followed by a molar amount of the alkylating agent with heating and stirring is repeated four times (for a total of five times) in order to effect the formation of compound (8).

Compound (9) is made by hydrolyzing the ketal, illustrated by the acetonide of formula (8). The hydrolysis is carried out as a single phase reaction using a polar, water soluble organic solvent, such as tetrahydrofuran. Preferably, the hydrolysis will be effected by means of a 10% solution of water in trifluoroacetic acid. The solution of the acetonide of formula (8) in organic solvent and aqueous acid solution are stirred for up to 3 hours, preferably one hour at a slightly elevated temperature, approximately 25°–70° C. preferably about 50° C. The solvent is then evaporated and residual acid removed by azeotropic distillation using a solvent such as toluene.

The aldehyde (10) is made by treating diol (9) with an oxidant, preferably one such as lead tetraacetate, in a solvent best illustrated by chloroform. A slight molar excess of lead tetraacetate is used to effect the reaction. The mixture is stirred at about ambient temperature for up to 4 hours, preferably about 2 hours, at which time the excess lead tetraacetate is quenched by addition of ethylene glycol followed quickly by the addition of a substantial amount of water. The resulting crude aldehyde is recovered by conventional means and may be used without further purification directly in the next step.

To effect the formation of the amine of formula (11), the appropriate amine hydrochloride, such as, for example, a commercially available secondary amine hydrochloride is dissolved in an alcohol, preferably methanol, to which solution is added a two-thirds molar amount of anhydrous sodium acetate. This mixture is stirred for about an hour at ambient temperature and the resulting sodium chloride is filtered off. The methanol solution is then added to the crude aldehyde of formula (10) from the preceding paragraph. A second solvent, preferably tetrahydrofuran, is then added to this mixture followed by molecular sieves. To this mixture is then added a reducing agent, preferably sodium cyanoborohydride, in a slight molar excess, and the mixture stirred at a slightly elevated temperature, preferably about 40° to about 60° C., for up to 3 days. This product (11) is then converted to the acid addition salt of formula (I) where $R^5$ is hydrogen by the addition of the appropriate acid such as hydrochloric acid in an organic solvent.

Alternatively, when $R^5$ is not hydrogen, the quaternary ammonium compound is then prepared by condensing an alkylating agent into a reaction vessel containing the amine material (11), after which the reaction vessel is sealed and heated to between about 50° and about 100° C., preferably about 70° C., for about 1 to about 5 days, preferably about 2 days. This procedure affords the tetraalkylammonium chloride product of Formula I.

Furthermore, when n is 1 and $R^1$ and $R^2$ are not the same, the compounds of Formula (I) can be prepared by the flowchart of Reaction Scheme III which follows.

In this Reaction Scheme, $R^1$ and $R^2$ can be the same or different, and $R^5$ is not aryl. The 1,3:4,6-di-O-benzylidine-D-mannitol of formula (12) is commercially available and is converted to the di-O-benzyl ether of formula (13) by the action of between 5 and 15, preferably about 10, molar equivalents of potassium hydroxide in benzylchloride at about 120° to about 160° C., preferably about 140°, for up to 5 hours, preferably 3 hours. This, in turn, is then hydrolyzed to the 2,5-di-O-benzyl-D-mannitol of formula (14) with aqueous acid in ethanol of pH between 0 and about 4, preferably about 1.5, at reflux for up to 10 hours, preferably about 5 hours.

The central hydroxyls of compound (14) were protected as a ketal, such as the acetonide of compound (15), by the reaction of compound (14) with a ketone under the influence of an acidic copper catalyst. Thus, compound (14) was dissolved in acetone and treated with 0.5 molar equivalents of copper sulfate and a slightly greater amount of sulfuric acid, preferably about 1.2 times that amount.

The two terminal hydroxyls of compound (15) were converted to the ethers of formula (16) by the action of an alkali base such as potassium tert-butoxide or more preferably potassium hydroxide in an appropriate high boiling solvent such as xylene, mesitylene or the like. To this is added an alkylating agent of the desired chain length and degree of unsaturation and the mixture is heated between about 100° and about 200° C., more preferably about 140° for up to 20 hours, preferably about 4 hours.

The two benzyl groups of compound (16) are then removed by catalytic hydrogenolysis in an appropriate solvent such as a mixture of tetrahydrofuran and methanol. A transition metal catalyst such as 10% palladium on carbon is used. The reaction is carried out in an appropriate hydrogenolysis device, in this instance with heating to about 60°

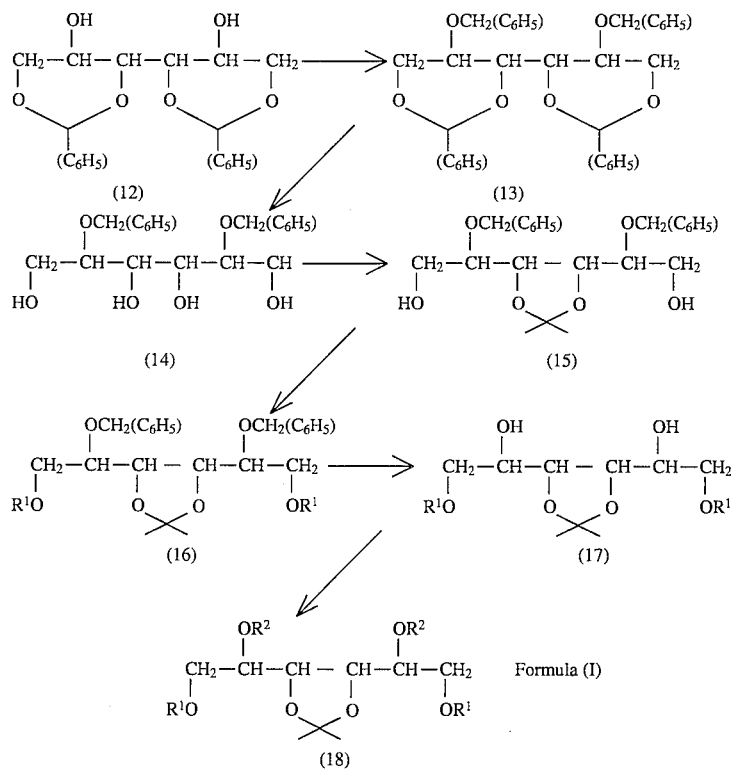

to about 80° C., for about 48 hours under about 60 psi of hydrogen.

The diol of formula (17) obtained from the preceding hydrogenolysis is etherified in the same manner described above for preparing compound (16).

Once the tetrasubstituted D-mannitol-3,4-ketal of formula (18) is obtained, it is converted to Formula I by the series of steps recited above for conversion of formula (8) to the compounds of Formula I.

Those compounds wherein n is 2–8 are prepared from the corresponding triol. The schematic for this reaction sequence is set forth in Reaction Scheme IV which follows. This scheme may also be used for preparing compounds where n is 1.

REACTION SCHEME IV

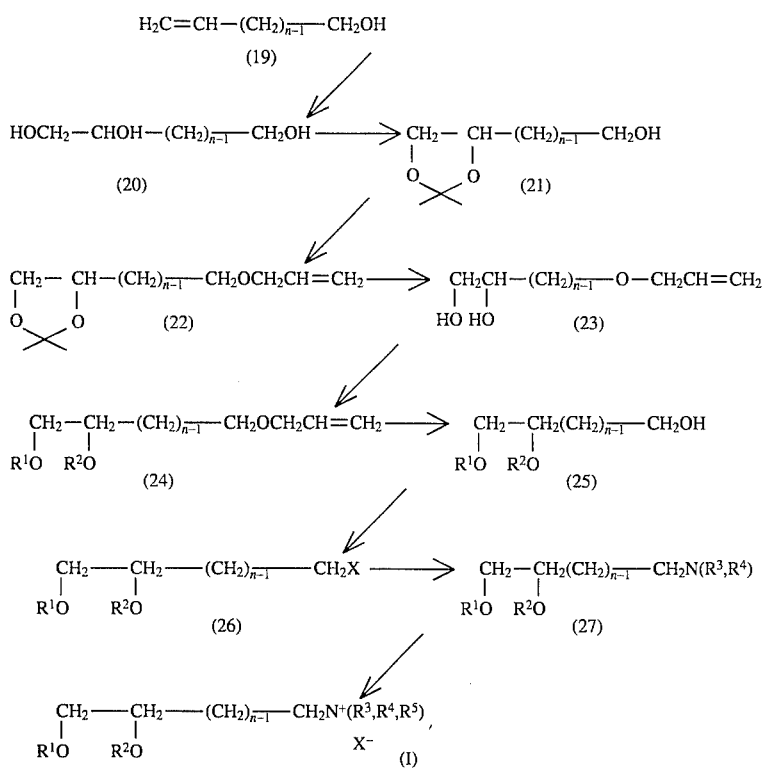

aprotic solvent, such as dimethylformamide. A strong base, such as sodium hydride (an equal molar amount), is added to the alcohol which is stirred at ambient temperature for a set period and then warmed to between about 80° and about 100° C. for an equal period. Allyl chloride, in about a 50% molar excess, is then added at the elevated temperature with stirring. Stirring and heating is continued for another approximately 30 to 120 minutes, preferably about 60 minutes. The product of formula (22) is then extracted and further purified by chromatographic means.

The ketal of compound (22) is then hydrolyzed by means of a dilute solution of a strong acid, for example, 1N HCl, the reaction being carried out in a polar solvent, such as methanol, ethanol, or the like. Some heat is added to the reaction mixture to effect the hydrolysis. Preferably, a solution is heated to about 50° C. for about 2 hours.

In this reaction scheme, $R^1$ and $R^2$ are the same, X is a leaving group, $X^-$ is an anion which may optionally correspond to the leaving group X, and n can be 1 to 8.

The compounds of formula 20 are known in the literature or may be purchased from a chemical supply house or may be prepared by the action of osmium tetroxide and trimethylamine-N-oxide on the appropriate alkenol of formula (19) in aqueous acetone/tert-butanol at room temperature for up to 48 hours, preferably about 20 hours.

The ketal of formula 21, preferably the acetonide, is prepared by dissolving the appropriate triol in acetone with the addition of a small amount of concentrated sulphuric acid. This reaction may be effected by stirring the solution for up to about 4 hours at room temperature, preferably about 2 hours. The resulting ketal is then recovered by some standard separatory means.

The unprotected primary hydroxyl group of compound (21) is then protected by forming an allyl ether. This reaction is carried out by dissolving the alcohol in a dry dipolar The diol of formula (23) is converted to the diether of formula (24) in the same manner as described above for conversion of formula (21) to formula (22). Here again the etherfication carried out in a dry dipolar aprotic solvent, such as dimethylformamide, using a strong base, such as sodium hydride, and the p-toluenesulfonate ester or halide of the appropriate chain length and degree of unsaturation. The reaction is repeated twice using a one molar equivalent of alkylating agent each time. As described previously, the reaction is effected at an elevated temperature, preferably between about 50° and about 150° C., more specifically at about 90° C.

The allyl ether of formula (24) is then hydrolyzed by means of Wilkinson's catalyst [tris(triphenylphosphine)rhodium chloride] in an acid medium. The solvent should be a polar solvent such as ethanol, preferably with a co-solvent such as tetrahydrofuran. The triether/catalyst mixture is refluxed for several hours, preferably about 3 hours, at which time additional acid (1N HCl) is added and refluxing continued for several more hours (approximately 3 to 4). These conditions effect hydrolysis of the allyl ether.

The alcohol of formula (25) is then converted to the amine by first creating an intermediate p-toluenesulphonate ester of formula (26) to which is added a dialkylamine to effect formation of the amine compound. By way of illustration, the alcohol is dissolved in a suitable solvent, such as pyridine, to which is added p-toluenesulphonyl chloride. This mixture is stirred overnight at ambient temperature, then poured into ice water and the product (26) recovered by extractive means. The crude product is immediately dissolved in a dialkylamine, such as dimethylamine, and placed in a sealed container at between about 25° and about 100° C., preferably about 70° C., for about 1 day to effect formation of the trialkylamine of formula (26).

The trialkylamine is most conveniently converted to an acid addition salt, preferably a hydrochloride salt, as a means of isolating the product.

The quaternary ammonium product Formula I is then prepared in the same manner as described hereinabove for the conversion of formula (4) to Formula I.

Alternatively, compounds of Formula I can be prepared by the reaction of compounds of formula (26) with the appropriate tertiary amine. This is particularly useful in the synthesis of compounds of Formula I wherein $R^5$ is aryl and where the positively charged nitrogen and two or three of $R^3$, $R^4$, and $R^5$ are combined to form one or two rings. For example, a solution of (26) and quinuclidine in dichloromethane was sealed in a pressure reactor and heated between about 50° and 150° C., preferably about 100° C., for up to 5 days, preferably about 2 days. This resulted in the formation of a compound of Formula I containing a bicyclic ammonium group.

V. PREPARATIONS AND EXAMPLES

Preparation 1

(S)-3-Dimethylamino-1,2-propanediol (of formula (3))

1,2-Isopropylidene-sn-glycerol 3-tosylate (10 g) was placed in a Parr pressure reactor and the entire apparatus was cooled to 0° C. Dimethylamine (approx. 10 ml) was condensed into the reactor and the vessel was sealed. The mixture was heated under pressure for 2 days. The reaction vessel was cooled to 0° C. and opened. The excess dimethylamine was allowed to evaporate and the residue was dissolved in methanol (100 ml) containing concentrated hydrochloric acid of pH 3, and the mixture was heated at reflux for 2 hours. After removal of the solvent in vacuo, the residue was partitioned between concentrated NaOH (5 ml, 10M) and tetrahydrofuran (100 ml). The tetrahydrofuran layer was evaporated to afford the title compound as a pale yellow oil.

$[\alpha]_D^{25}=-26.8°$ )1% $CH_3CO_2H/H_2O$); $^1H$ NMR (90 MHz, $CDCl_3$ δ 4.0–3.3 (m, 3H), 2.9 (OH), 2.8–2.0 (m, 8H).

Preparation 2

In accordance wtih Reaction Scheme I, a mixture of 3-(dimethylamino)-1,2-propanediol (1.19 g, 10 mmol), potassium tert-butoxide (3.36 g, 30 mmol) and oleyl toluenesulfonate (12.7 g, 30 mmol) in xylenes (50 ml) was stirred at room temperature under house vacuum (approx. 30 torr) for 0.5 hour. The mixture was heated to 50° C. and stirred for an additional 0.25 hour. The vacuum was removed and the reaction vessel was filled with nitrogen gas to room pressure (approx. 1 atm.). The temperature was increased until the reaction boiled (approximately 140° C.) and the mixture was stirred at reflux for 3 hours. The mixture was diluted with hexane (100 ml) and extracted with water (2×50 ml). The organic layer was concentrated, applied to a column of silica gel (150 g) packed in hexanes in ether (1:2), then eluted with the same solvent mixture to give the title compound (4.5 g) as an oil.

Proceeding in a similar manner, but substituting for 3(dimethylamino)-1,2-propanediol the appropriate precursor, the following compounds were made:

(±) N-methyl-N-(2,3-di-hexadecyloxy)-prop-1-yl-pyrrolidine;

(±) N-methyl-N-(2,3-di-hexadecyloxy)-prop-1-yl-piperidine;

(±) N-methyl-N-(2,3-di-hexadecyloxy)-prop-1-yl-morpholine; and (S)-N-(2,3-Di-(9-(Z)-octadecnyloxy))prop-1-yl-N,N,-dimethylamine.

Proceeding in a similar manner, but substituting for the p-toluenesulfonate of oleyl alcohol the appropriate alkylating agent, the following compound was made:

(±) N-(2,3-dihexadecyloxy)-prop-1-yl-N,N-dimethylamine.

Proceeding in a similar manner, but substituting for the p-toluenesulfonate of oleyl alcohol the appropriate precursor, the following compound is made:

N-(2,3-di-(dec-2-ynyloxy))-prop-1-yl-N,N-dimethyl-amine.

Preparation 3

1,2:3,4:5,6-Triisopropylidine-D-Mannitol (of formula 6))

Perchloric acid (3.5 ml, 70%) was added to a mixture of D-mannitol (100 g) and 2,2-dimethoxypropane (700 ml) in acetone (100 ml). After stirring this mixture at room temperature for 18 hours, sodium bicarbonate (5 g) was added to the solution. This mixture was stirred at room temperature for 1 hour and then filtered. The filtrate was concentrated to ½ of the original volume and diluted with water (500 ml) to give the title compound.

Preparation 4

D-Mannitol-3,4-Acetonide (of formula (7))

1,2:3,4:5,6-Triisopropylidine-D-Mannitol (90 g) was dissolved in 70% acetic acid (250 ml) and heated at 45° C. for 1.5 hours. The mixture was concentrated in vacuo to an oil. This oil was resuspended in toluene (150 ml) and again concentrated in vacuo. The resulting oil was dissolved in ethylacetate (400 ml) and cooled to −5° C. The title compound crystallized from this mixture.

Preparation 5

1,2,5,6-Tetraoleyl-D-mannitol-3,4-acetonide (of formula (8))

D-Mannitol-3,4-acetonide (5.0 g, 22.52 mmol) was dissolved in dimethylformamide (200 ml, distilled from calcium hydride under reduced pressure). To this solution was added sodium hydride (1.08 grams, 22.52 mmol, 50% oil dispersion) and the mixture was heated to 50° C. and stirred for 1 hour (mechanical stirrer required). To the resulting mixture was added the toluenesulfonate of oleyl alcohol (9.5 grams, 22.52 mmol). The temperature was increased to 90° C. and stirring was continued for 1 hour.

The sequence of addition of sodium hydride (same amount) and stirring 1 hour, then addition of oleyl tosylate (same amount) and stirring 1 hour, all at a constant 90° C., was repeated 4 more times (total of 5 times). The reaction mixture was allowed to cool to room temperature then poured slowly into a saturated solution of sodium chloride (500 ml). The resulting mixture was extracted with hexanes (3×250 ml), dried (potassium carbonate) and concentrated. The crude product was chromatographed over silica gel (1000 grams) eluting with a gradient of from 0 to 5% diethyl ether in hexanes to give 13.93 grams of the title compound as a viscous oil.

Proceeding in a similar manner, but substituting for the toluenesulfonate of oleyl alcohol the appropriate precursor, the following compounds were made:
1,2,5,6-tetradecyl-D-mannitol-3,4-acetonide;
1,2,5,6-tetrahexadecyl-D-mannitol-3,4-acetonide;
1,2,5,6-tetradocosyl-D-mannitol-3,4-acetonide;
1,2,5,6-tetra-(4-Z-decenyl)-D-mannitol-3,4-acetonide.

Preparation 6

1,2,5,6-Tetraoleyl-D-mannitol (of formula (9))

To a solution of 1,2,5,6-tetraoleyl-D-mannitol-3,4-acetonide (24.0 grams, 19.62 mmol) in tetrahydrofuran (100 ml) was added $H_2O$:trifluoroacetic acid (1:9, 100 ml). This solution was stirred for 1 hour at 50° C., then concentrated to an oil by rotary evaporation. Toluene (200 ml) was added and evaporated to azeotropically remove the residual acid. The crude material was dissolved in diethyl ether (100 ml) and a saturated solution of ammonium hydroxide in water (10 ml) was added. This mixture was stirred for 2 hours and then the ether phase was washed two times with water, dried (magnesium sulfate) and concentrated. The crude product was suitable for further reaction; a small portion was purified by column chromatography over silica gel (10% ethyl acetate/hexanes) to give an analytical sample of the desired diol as a viscous oil.

Proceeding in a similar manner, but substituting for the 1,2,5,6-tetraoleyl-D-mannitol-3,4-acetonide of formula (8) the appropriate precursor, the following compounds were made:
1,2,5,6-tetradecyl-D-mannitol;
1,2,5,6-tetrahexadecyl-D-mannitol;
1,2,5,6-tetradocosyl-D-mannitol;
1,2,5,6-tetra-(4-Z-decenyl)-D-mannitol; and
1,6-didecyl-2,5-dihexadecyl-D-mannitol.

Preparation 7

(S)-N-(2,3-Di-(9-(Z)-octadecenyloxy) prop-1-yl-N,N,-dimethylamine (of formula (11))

The crude oil 1,2,5,6-tetraoleyl-D-mannitol described in the previous example, was dissolved in chloroform (500 ml) and lead tetraacetate (11.8 g, 26.0 mmol) was added. This mixture was stirred for 2 hours and then ethylene glycol (5 ml) was added followed quickly by water (100 ml). The water phase was drawn off and the organic phase was washed once with saturated sodium chloride solution, dried (magnesium sulfate), and concentrated to an oil to give the crude aldehyde of formula (10) which was used immediately in the next step.

To a solution of dimethylamine hydrochloride (35.5 g, 435 mmol) in methanol (150 ml) was added anhydrous sodium acetate (24 g, 282 mmol). The mixture was stirred for 1 hour and then the resulting sodium chloride was filtered off and the clear methanol solution added to the crude aldehyde. Tetrahydrofuran (150 ml) was added followed by 3 angstrom molecular sieves (about 20 g). Sodium cyanoborohydride (1.5 g, 23.9 mmol) was added and the mixture was stirred at 50° C. for three days. The crude reaction mixture was filtered through Celite (washing with 1:1 tetrahydrofuran) and the solution was strongly acidified with 1N HCl and stirred for ½ hour. The solution was then made strongly basic with 10% NaOH and extracted with diethyl ether (3×200 ml). The crude product was purified by column chromatography over silica gel using a gradient of 0 to 10% methanol in chloroform to give the captioned dimethylamino product as a viscous oil.

The hydrochloride salt of the title compound was prepared by dissolving the foregoing product (100 mg) in ether (10 ml) and adding three drops of ethyl acetate saturated with HCl gas. The resulting solution was concentrated and placed under high vacuum for 24 hours. The resulting product was a gummy solid.

Proceeding in a similar manner, but substituting for the 1,2,5,6-tetraoleyl-D-mannitol of formula (9) the appropriate precursor, the following compounds are made:
(S) N-(2,3-di-decyloxy)-prop-1-yl-N,N-dimethylamine;
(S) N-(2,3-di-hexadecyloxy)-prop-1-yl-N,N-dimethylamine;
(S) N-(2,3-di-(4-(Z)-decenyloxy)-prop-1-yl-N,N-dimethylamine; and
(S) N-(2,3-di-docosyloxy)-prop-1-yl-N,N-dimethylamine.

Preparation 8

2,5-Di-O-benzyl-1,3:4,6-di-O-benzylidene-D-mannitol (of formula (13))

Powdered potassium hydroxide (37 g) was added to 1,3:4,6-di-O-benzylidene-D-mannitol (10 g) dissolved in benzyl chloride (64 ml). The mixture was heated at 140° C. for 3 hours, then cooled and diluted with water (200 ml). Extraction with chloroform, followed by washing with water and evaporation gave a solid, which was crystallized from petroleum ether to give the captioned compound, m.p. 102°–3° C.

Preparation 9

2,5-Di-O-benzyl-D-mannitol (of Formula 14)

2,5-Di-O-benzyl-1,3:4,6-di-O-benzylidene-D-mannitol (10.9 g) dissolved in ethanol (150 ml) and water (22 ml) was treated with 1M HCl (7 ml). After refluxing this mixture for 4.5 h, the reaction was cooled and quenched with barium carbonate, then evaporated to dryness. The solid residue was triturated with hot ethyl acetate, which was then evaporated to give the captioned compound, m.p. 116°–117° C.

Preparation 10

2,5-Dibenzyl-D-mannitol-3,4-acetonide (of formula (15))

2,5-Dibenzyl-D-mannitol (48 g, 133 mmol) dissolved in dry acetone (1000 ml) was treated with copper(II)sulfate (10 g, 62.6 mmol) and concentrated sulfuric acid (2 ml). After stirring at room temperature for 48 hours, the mixture was quenched by the addition of solid sodium carbonate, followed by stirring for 3 hours. The reaction mixture was filtered and concentrated and the residue was crystallized from hexane ethyl acetate to give 38.0 g of the title compound, m.p. 73°–74° C.

Preparation 11

2,5-Dibenzyl-1,6-didecyl-D-mannitol-3,4-acetonide (of formula (16))

A mixture of 2,5-dibenzyl-D-mannitol-3,4-acetonide (10.0 g, 25 mmol), powdered potassium hydroxide (23 g) and decyl bromide (40 ml) in xylene (300 ml) was heated at reflux for 4 hours. The mixture was cooled, diluted with hexanes (300 ml), decanted from excess salts and applied to a column of dry silica gel (1 Kg). Elution with hexanes followed by a gradient of 0 to 50% ether in hexanes gave the title compound as an oil.

Preparation 12

1,6-Didecyl-D-mannitol-3,4-acetonide (of formula (17))

Dibenzyl compound of Example 6 ) 6.0 g, 8.8 mmol) was dissolved in tetrahydrofuran/methanol (1:1, 100 ml). After bubbling nitrogen through for several minutes, 10% palladium on carbon (1 gram) was added and the mixture was shaken at 70° C. under 60 psi hydrogen for 48 hours. The mixture was filtered and concentrated to give the title compound (4.3 g) as a white solid; m.p. 36°–39° C.

Preparation 13

1,6-Didecyl-2,5-dihexadecyl-D-mannitol-3,4-acetonide (of formula (18))

1,6-Didecyl-D-mannitol-3,4-acetonide (4.3 g, 8.57 mmol) and bromohexadecane (7.84 g, 25.7 mmol)were dissolved in xylene (40 ml) and KOH (5.0 grams) was added. This mixture was stirred at reflux for 1.5 hours. After cooling the mixture was decanted onto a column of silica gel (dry, 200 g), then eluted with hexanes followed by 3% ether in hexanes to give the title compound (7.3 g) as an oil.

Preparation 14

1,2,10-Decanetriol (of formula (20))

9-Decan-1-ol (25 g, 160 mmol) was dissolved in a solution made up of t-butanol (100 ml), acetone (90 ml) and water (10 ml). To this solution was added trimethylamine-N-oxide (26.6 g, 240 mmol) and 2 ml of a solution of osmium tetroxide (500 mg) in t-butanol (25 ml). The resulting solution was stirred 20 hours under nitrogen then 10% sodium bisulfite was added (50 ml). The mixture was concentrated, then taken up in trichloromethane and washed 2 times with water, dried with $Na_2SO_4$ and concentrated to give 1,2,10-decanetriol as an oil. This material was used without further purification in preparation of the corresponding acetonide (of formula 21).

Preparation 15

1,2,6-Hexanetriol-1,2-acetonide (of formula (21))

1,2,6-Hexanetriol (31 g, 0.23 mmol) was stirred with acetone (150 ml). To this mixture was added concentrated sulfuric acid (5 drops). The resulting solution was stirred for 2 hours at room temperature. The reaction solution was diluted with diethyl ether, washed with saturated sodium bicarbonate solution, dried (magnesium sulfate) and concentrated to give the title compound (31 g) as a clear oil.

Proceeding in a similar manner, but substituting for the 1,2,6-hexanetriol the appropriate precursor, the following compounds were made:
1,2,4-butanetriol-1,2-acetonide;
1,2,10-decanetriol-1,2-acetonide.

Preparation 16

1,2-Hexanediol-1,2-acetonide-6-allyl ether (of formula (22))

The acetonide of Preparation 15 (30 g, 172 mmol) was dissolved in dry dimethylformamide (500 ml). To this solution was added sodium hydride (8.28 g, 172 mmol, 50% oil dispersion) and the mixture was stirred for ½ hour at room temperature then warmed to 90° C. over ½. To this mixture was added allyl chloride (21 ml, 258 mmol) and the stirring was continued for 1 hour. After cooling, the mixture was poured into water and extracted with ether (2×100 ml). The combined ether extracts were washed with brine, dried (magnesium sulfate) and concentrated. Chromatography over silica gel (10% ether in hexanes) gave the title product as a clear oil; bp=70° C. at 0.01 mmHg.

Proceeding in a similar manner, but substituting for 1,2,6-hexanetriol-1,2-acetonide the appropriate precursor, the following compounds were made:
1,2-butanediol-1,2-acetonide-4-allyl ether;
1,2-decanediol-1,2-acetonide-10-allyl ether.

Preparation 17

1,2-di-hydroxy-hexan-6-allyl ether (of formula (23))

In ethanol (100 ml) was dissolved 1,2-hexanediol-1,2-acetonide-6-allyl ether (20 g, 93.9 mmol) to which was added 20 ml of 1N HCl. The solution was then heated to 50° C. for 2 hours. The resulting solution was concentrated, then taken up in chloroform (100 ml) and washed with brine (2×10 ml), dried (sodium sulfate) and concentrated to give the title compound as a clear oil.

Proceeding in a similar manner, but substituting for 1,2-hexanediol-1,2-acetonide-6-allyl ether the appropriate precursor, the following compounds were made:
1,2-di-hydroxy-butan-4-allyl ether;
1,2-di-hydroxy-decane-10-allyl ether.

Preparation 18

1,2-Di(9-(Z)-octadecenyloxy)-hexan-6-allyl ether (of formula (24))

The diol of Preparation 17 (3.45 g, 19.83 mmol) was dissolved in dry dimethylformamide (60 ml). To this solution was added sodium hydride (951 mg, 19.8 mmol). The mixture was heated to 90° C. and oleyl tosylate (8.37 g, 19.8 mmol) was added. Stirring was continued for 1 hour at which time a second equivalent of sodium hydride (951 mg, 19.8 mmol) was added. After 15 minutes a second equivalent of oleyl tosylate (8.37 g, 198. mmol) was added and stirring was continued for 1 hour. The reaction mixture was poured into water and extracted with ether (2×100 ml). Column chromatography over silica gel (0 to 5% ether/hexanes) gave 3.5 g of the title compound as a clear oil.

Proceeding in a similar manner, but substituting for 5,6-hydroxy-hexan-1-allyl ether the appropriate precursor, the following compounds were made:
1,2-di-(9-Z-octadecenyloxy)-butan-4-allyl ether;
1,2-di-(9-Z-octadecenyloxy)-decan-10-allyl ether.

Preparation 19

1,2-Di(9-(Z)-octadecenyloxy)-hexan-6-ol (of formula (25))

The triether of Preparation 18 (3.20 g, 4.74 mmol) was dissolved in ethanol/tetrahydrofuran (1:1, 30 ml) and Wilkinsons catalyst (tris(triphenylphosphine)rhodium chloride, 200 mg) was added followed by 0.1N HCl (1 ml). This mixture was refluxed for 3 hours then 1N HCl (5 ml) was added and refluxed 4 hours. The solution was cooled and concentrated. Diethyl ether was added and washed with brine, dried (magnesium sulfate), concentrated and chromatographed over silica gel (5 to 50% ether in hexanes) to give 2.56 g of the title alcohol as an oil.

Proceeding in a similar manner, but substituting for 1,2-di(9-Z-octadecenyloxy)-6-allyloxyhexane the appropriate precursor, the following compounds were made:
1,2-di-(9-Z-octadecenyloxy)-butan-4-ol;
1,2-di-(9-Z-octadecenyloxy)-decan-10-ol.

Preparation 20

(%) N-(5,6-di-(9-(Z)-octadecenyloxy))-hex-1-yl-N,N-dimethyl amine (of formula (27))

The substituted hexan-6-ol from Preparation 19 (2.50 g, 3.94 mmol) was dissolved in pyridine (20 ml) and p-toluenesulfonyl chloride (0.90 g, 4.73 mmol) was added. This mixture was stirred overnight at room temperature then poured into ice water and stirred ½ hour. The resulting mixture was extracted with ether and the ether phase was washed with 0.1N HCl, dried (magnesium sulfate) and concentrated. This crude intermediate was immediately dissolved in dimethylamine and placed in a sealed tube at room temperature for 20 hours. The tube was cooled to 0° C. and opened. The dimethylamine was allowed to evaporate under a stream of nitrogen. Column chromatography of the crude product over silica gel (0 to 5% methanol in chloroform) gave the title product as a very thick oil. The hydrochloride was prepared as described in Preparation 7. This was also an oil, NMR (300 MHz, CDCl$_3$) 5.40–5.30 (m, 4H), 3.65–3.50 (m, 1H), 3.50–3.30 (m, 6H), 3.05–2.90 (m, 2H), 2.79 (s, 6H), 2.10–1.65 (m, 11H), 1.65–1.45 (m, 8H), 1.45–1.15 (m, 44H), 0.95–0.80 (m, 6H).

In a similar manner, but substituting the appropriate starting material, the following compounds were prepared:

(±) N-(3,4-di-(9-(Z)-octadecenyloxy))-but-1-yl-N,N-dimethylamine hydrochloride, oil, NMR, (90 MHz, CDCl$_3$) 5.33 (t, J=5 Hz, 4H), 3.85–3.15 (m, 18H), 2.20–1.80 (m, 8H), 1.70–1.00 (m, 50H), 0.88 (t, J=7 Hz, 6H);

(±) N-(9,10-di-(9-(Z)-octadecenyloxy))-dec-1-yl-N,N-dimethylamine hydrochloride, wax, NMR, (90 MHz, CDCl$_3$) 5.34 (t, J=5 Hz, 4H), 4.65–4.25 (m, 9H), 2.81 (s, 3H), 2.75 (s, 3H), 2.20–1.75 (m, 8H), 1.75–1.00 (m, 62H), 0.88 (t, J=7 Hz, 6H).

Preparation 21

2,3-Di-(9-(Z)-octadecenyl)propan-1-ol (of formula (25))

Crude 2,3-di(9-(Z)-octadecenyl)propanol of formula (10) from Preparation 7 (10.0 g, 16.9 mmol) was dissolved in tetrahydrofuran/methanol (1:1, 200 ml) and cooled to 0° C. Sodium borohydride (3.13 g, 85.0 mmol) was added and the mixture was stirred overnight. The solution was acidified with 1N HCl to pH=2, diluted with ether, washed with water, concentrated and column chromatographed (chloroform) to give the title compound as an oil.

Preparation 22

1,2-Di(9-(Z)-octadecenyloxy)-3-iodopropane (of formula (26))

The alcohol 2,3-di(9-(Z)-octadecenyl)propan-1-ol (5.0 g, 8.36 mmol) was dissolved in pyridine (50 ml) and p-toluenesulfonyl chloride (1.91 g, 10.0 mmol) was added. The solution was stirred for 24 hours then poured into ice water, extracted with ether and washed with 1N HCl until the aqueous layer remained acidic. The organic phase was dried (magnesium sulfate) and concentrated to give crude tosylate. The material was dissolved in methyl ethyl ketone (50 ml), sodium iodide (1.5 g, 10.0 mmol) was added and the solution was refluxed for 5 hours. The solvent was removed and the residue was taken up in ether and washed with water. The organic layer was concentrated and chromatographed to give the title compound as an oil.

EXAMPLE 1

(S) N-(2,3-Di-(9-(Z)-octadecenyloxy))-prop-1-yl-N,N,N-trimethylammonium chloride The dimethylamino product N-(2,3-di-(9-(Z)-octadecenyloxy))-prop-1-yl-N,N-dimethylamine (10 grams) was placed in a Parr pressure reactor and cooled to −78° C. Methyl chloride (about 50 ml) was condensed into the reaction vessel, which was then sealed and heated to 70° C. for 48 hours. The reaction vessel was cooled and opened and the methyl chloride allowed to evaporate under a stream of nitrogen. The crude product was crystallized from acetonitrile to give the title compound as an off-white solid, (S) N-(2,3-di-(9-(Z)-octadecenyloxy))-prop- 1-yl-N,N,N-trimethylammonium chloride, $[\alpha]_D^{25}$ −20.0° (CHCl$_3$);

Proceeding in a similar manner, but substituting for N-(2,3-di-(9-(Z)-octadecenyloxy))-prop-1-yl-N,N-dimethylamine the appropriate precursor, the following compounds are prepared:

(S) N-(2,3-di-decyloxy)-prop-1-yl-N,N,N-trimethylammonium chloride, m.p. 87°–88° C., $[\alpha]_D^{25}$ −26.5° (CHCl$_3$);

(S) N-(2,3-di-hexadecyloxy)-prop-1-yl-N,N,N-trimethylammonium chloride, $[\alpha]_D^{25}$ −23.4° (CH$_3$OH);

(S) N-(2,3-di-(4-(Z)-decenyloxy))-prop-1-yl-N,N,N-trimethylammonium chloride, wax, $[\alpha]_D^{25}$ 0° (CHCl$_3$);

(S) N-(2,3-di-docosyloxy)-prop-1-yl-N,N,N-trimethylammonium chloride, m.p. 161°–163° C., $[\alpha]_D^{25}$ −15.7° (CHCl$_3$);

(±) N-(2,3-di-(9-(Z)-octadecenyloxy)-prop- 1-yl-N,N,N-trimethylammonium chloride, m.p. 35°–38° C., NMR (300 MHz, CDCl$_3$) 5.35 (t, J=5 Hz, 4 H), 4.15–3.90 (m, 2H), 3.80–3.40 (m, 3.H), 3.49 (s, 9H), 3.43 (t, J=7 Hz, 4 H), 2.01 (m, 8H), 1.56 (m, 4H), 1.27 (m, 40H), 0.88 (t, J=7 Hz, 6HO);

(±) N-(2,3-dihexadecyloxy)-prop-1-yl-N,N,N-trimethylammonium chloride, m.p. 76°–78° C.,;

(±) N-methyl-N-(2,3-di-hexadecyloxy)-prop-1-yl-pyrrolidinium chloride, m.p. 71°–73° C.,;

(±) N-methyl-N-(2,3-di-hexadecyloxy)-prop-1-yl-piperidinium chloride, m.p. 111°–116° C.,;

(±) N-methyl-N-(2,3-di-hexadecyloxy)-prop-1-yl-morpholinium chloride, m.p. 118°–121° C.,;

(±) N-(5,6-di-(9-(Z)-octadecenyloxy)-hex-1-yl-N,N,N-trimethylammonium chloride, oil;

(±) N-(9,10-di-(9-(Z)-octadecenyloxy)-dec-1-yl-N,N,N-trimethylammonium chloride, oil, NMR (300 MHz, CDCl$_3$) 5.40–5.30 (t, J=t Hz, 4H), 3.70–3.30 (m, 9H), 3.46 (s, 9H), 2.10–1.90 (m, 8H), 1.85–1.65 (m, 2H), 1.60–1.20 (m, 50H), 0.88 (t, J=7 Hz, 6H);

(±) N-(3,4-di-hexadecyloxy)-but-1-yl-N,N,N-trimethylammonium chloride, m.p. 177°–179° C.,; and (S) N-(3-decyloxy-2-hexadecyloxy)-prop-1-yl-N,N,N-trimethylammonium chloride, m.p. 88°–90° C., $[\alpha]_D^{25}$ –24.7° (CHCl$_3$).

Proceeding in a similar manner, but substituting for N-(2,3-di-(9-(Z)-octadecenyloxy))-prop-1-yl-N,N-dimethylamine the appropriate precursor, the following compound is made:

) N-(2,3-di-(dec-2-ynyloxy))-prop-1-yl-N,N,N-trimethylammonium chloride.

EXAMPLE 2

(±) N-(2,3-Dihexadecyloxy)-prop-1-yl-N, N,N-trimethylammonium chloride

Dimethyl sulfate (187 g, 1.5 moles) was added dropwise to a solution of (±) N-(2,3-dihexadecyloxy)-prop-1-yl-N,N-dimethylamine (740 g, 1.3 moles) in toluene (2 L) at room temperature. After completion of the addition, the mixture was stirred for one additional hour at room temperature. This solution was extracted with saturated sodium chloride (2×500 mL) and the toluene layer was diluted with acetone (2 L) and cooled to 5° to give the title compound as a colorless solid, (±) N-(2,3-di-hexadecyloxy)-prop-1-yl-N,N,N-trimethylammonium chloride, m.p. 76°–78° C.

EXAMPLE 3

N-(2,3-Di-(9-(Z)-octadecenyloxy))-prop-2-yl-quinuclidinium chloride (Formula I)

The iodopropane of Example 14 (2.0 grams, 2.28 mmol) was dissolved in dichloromethane (1 ml) and quinuclidine (1.57 grams, 14.1 mmol) was added. The solution was sealed in a pressure reactor and heated to 100° C. for 48 hours. The crude product was chromatographed over a small plug of silica gel (0 to 5% methanol in chloroform) and then ion exchanged over Dowex 2-X8 (chloride form, eluting with methanol) to give the title compound, (S) N-(2,3-di-(9-(Z)-octadecenyloxy))-prop-1-yl-quinuclidinium iodide, m.p. 81°–83° C., $[\alpha]_D^{25}$ –33.5° (CHCl$_3$);

In a similar manner, but substituting the appropriate starting material, the following compounds are prepared:

N-(2,3-Di-(9(Z)-octadecenyloxy)-prop-1-yl-N-ethyl-N-ethyl-N-methyl-N-phenylammonium iodide;

N-(2,3-Di-(9(Z)-octadecenyloxy)-prop-1-yl-N-benzyl-N,N-dimethylammonium iodide;

N-(2,3-Di-(9(Z)-octadecenyloxy))-prop-1-yl-N-benzyl-N,N,N-triphenylammonium iodide;

N-(2,3-Di-(9(Z)-octadecenyloxy)-prop-1-yl-pyridinium iodide.

EXAMPLE 4

The following compositions illustrate the use of the instant compounds in pharmaceutical formulations.

1) Thirty-four mg of N-(2,3-di-(9(Z)-octadecenyloxy))-prop-1-yl-N,N,N-trimethylammonium chloride and 6.3 mg of 9-(1,3-dihydroxy-2-propoxymethyl) guanine dipalmitate were dissolved in chloroform/methanol (2:1:2 ml). Solvent was removed under a stream of nitrogen and placed in vacuo overnight. The dried film was suspended in 1 ml of 50 mM phosphate buffered saline, pH 7.4 and sonicated to clarity.

2) A topical formulation was prepared by dissolving 0.025 mg of fluocinolone acetonide [6α, 9α-difluoro-11β, 16α, 17α, 21-tetrahydroxypregna-1,4-diene-3,20-dione 16,17-acetonide] 0.25 grams of N-(2,3-di-( 9-(Z)-octadecenyloxy))-prop-1-yl-N,N,N-trimethyl ammonium chloride in 20 ml of dichloromethane. The solvent was evaporated under a stream of nitrogen gas until a dry film was obtained. The film mixture was placed under vacuum overnight to evaporate off the dichloromethane completely. The dry film was then suspended in 25 ml of 1% sodium chloride solution. The suspension was sonicated until visually clear.

3) Fluocinonide [6α, 9α-difluoro-11β, 16α, 17α, 21-tetrahydroxypregna-1,4-diene-3,20-dione, 16,17-acetonide-21-acetate] 0.025 grams and 1.0 grams of N-(2,3-di-(9-(Z)-octadecenyloxy))-prop-1-yl-N,N,N-trimethylammonium chloride were dissolved in 20 ml of dichlormethane which was then evaporated under a stream of nitrogen gas until a dry film was obtained. This film mixture was placed under vacuum overnight to evaporate off residual dichloromethane. The resulting film was suspended in 25 ml of 1% sodium chloride solution and sonicated until visually clear.

4) There was dissolved 160 mg N-(2,3-di-(9-(Z)-octadecenyloxy))-prop-1-yl-N,N,N-trimethylammonium chloride and 20 mg butoconzaole nitrate [1-[4-(4-chlorophenyl)-2-(2,6-dichlorophenylthio)-n-butyl] imidazole nitrate] in 2 mls of chloroform. The chloroform was removed under a stream of nitrogen and the residue was placed under vacuum overnight to remove residual chloroform. The resulting film was suspended in 2 mls of purified water by hand shaking and vortexing.

5) Diarachidoylphosphatidyl choline, 60 mg, and 5.4 mg N-(2,3-di-(9-(Z)-octadecenyloxy))-prop-1-yl-N,N,N-trimethylammonium chloride was dissolved in 2 ml of chloroform which was removed under a stream of nitrogen and placed under vacuum overnight to remove residual solvent. The resulting film was suspended in 2 mls of purified water containing 20 million units of beta-interferon by gentle trituration to avoid excessive foaming.

6) Thirty mg of N-(2,3-di-(9-(Z)-octadecenyloxy))-prop-1-yl-N,N,N-trimethylammonium chloride and 3 mg of 6-O-stearoyl-N-acetyl-muramyl-L-α-aminobutyryl-D-isoglutamine were dissolved in chloroform. A nitrogen stream was used to remove the majority of the solvent, the residual solvent being removed under vacuum. The resulting film was suspended in 1 ml of purified water and treated with ultrasound until clear.

7) Distearoylphosphatidyl choline, 2.22 mg, 1 mg N-(2, 3-di-(9-(Z)-octagecenyloxy))-prop-1-yl-N,N,N-trimethylammonium chloride and 0.23 mg of cholesterol were dissolved in 1 ml chloroform. Solvent was removed under a stream of nitrogen and the residue placed under vacuum overnight. The dried film was suspended in 6 mM phosphate buffered saline containing 8% Triton X-100 (0.5 ml). To this was added 50 μg of lectin affinity column purified bovine herpes antigen. Then 1 ml of packed BioBeads was added (to remove Triton X-100) and shaken gently for 2 hours at 55° C. after which the BioBeads were decanted.

8) 14 Micromoles of dioleoylphosphatidyl choline and 6 micromoles of N-(2,3-di-(9-(Z)-octadecenyloxy))-prop-1-yl-N,N,N-trimethylammonium chloride were dissolved in 2 ml of chloroform and then dried down under a stream of nitrogen. The resulting dried film was placed under vacuum for ½ hour, after which the film was then dissolved into 1 ml of cyclohexane, transferred to a 100 ml round-bottomed flask and frozen on dry ice. The flasks were then attached to a lyophilization apparatus and the cyclohexane removed. Murine gamma interferon solution [0.2 ml (500,000 units/ml) was suspended in a buffer containing 10 mM monopotassium phosphate, 2 mM sodium chloride and 3 mM potassium chloride (adjusted to pH 8.0 with potassium hydroxide)] was then added to the lyophilized lipids which caused formation of liposomes. The liposomes were then diluted to a convenient concentration with more phosphate buffer as needed.

In a similar manner other concentrations of drug in liposomes can be prepared. By varying the amount of aqueous solution added to the film, the concentration of drug in the final liposome formulation can be varied between 0.05 and 10% by weight.

9) Two types of lipid were used and compared in the presence of three different buffers.

| Lipids: | 1) | DOTMA; 13 mg |
|---|---|---|
|  | 2) | DOPO/DOPC, 7.3 (w/w); 13 mg |
| Buffers: | 1) | 0.02 M phosphate; 0.9% NaCl |
|  | 2) | 0.02 M isotonic glucose |
|  | 3) | deionized water |

Lipid stock solutions were prepared in chloroform at 20 mg/ml. A 0.01M stock solution of ketorolac was prepared in methanol. The lipid and drug were mixed into a glass vial and the solvent was removed under a stream of nitrogen gas. The dried films were evacuated overnight on a vacuum pump to remove traces of solvent. Each of the drug/lipid films was reconstituted by vortexing with one of the buffers. 0.15 µl of the liposome suspension was removed and centrifuged at 100,000×g in a Beckman Airfuge. Only the liposome formulations containing NaCl (buffer 1) gave pellets after centifugation. The supernatants were withdrawn from these preparations and assayed in a UV spectrophotometer (peak absorbance 319 nm). The results indicated that the DOTMA liposomes entrapped more than 80% of the drug, whereas, the conventional DOPC/DOPG liposome entrapped less than 5% of the drug.

Another DOTMA/ketorolac formulation was prepared identical to the above, except that 0.1 mg of the rhodamine phosphatidyl ethanolamine (in chloroform) was added to the mixture before solvent removal under nitrogen. The resulting fluorescent liposomes were applied to dissected rabbit cornea for 2 hours, washed with isotonic saline, and prepared for cryostat sectioning. Thin sections were cut and observed by fluorescent microscopy. Fluorescence was observed on the surface of the cornea indicated the liposomes adhered to rabbit cornea.

EXAMPLE 5

Intracellular Introduction of Oligoribonucleotides

Oligoadenylates of the general structure $ppp(A2'p)_nA$, n=2, are referred to as "2-5A". 2-5A molecules are well known, to those skilled in the art, to bind to an intracellular endonuclease resulting in activation of the endonuclease with subsequent cleavage of ribosomal and messenger RNA, resulting in inhibition of protein synthesis. However due to the highly negatively-charged nature of the 2-5A oligonucleotides, they do not cross the intact cell membrane and thus are inactive when added to intact, nonpermeabilized cells. A calcium phosphate coprecipitation technique can be employed to artificially introduce 2-5A into cells, which can be monitored by inhibition of protein synthesis. Thus $10^{-5}$ to $10^{-9}$ M 2-5A was added to a solution of 120 mM $CaCl_2$, which was then added dropwise into bubbled Hepes buffered saline, pH 7.05 (8.0 g NaCl, 0.37 g KCl, 0.125 g $Na_2HPO_4$"$2H_2O$, 1.0 g glucose, and 5.0 g Hepes per liter). A final sample volume of 0.5 ml was added to quadruplicate wells of Costar 24 well plates containing confluent Vero or $L_{929}$ cells. After 45 minutes at room temperature, an additional 0.5 ml of media was added to each well and incubated an additional 90 minutes at 37° C. The solutions were then removed by aspiration, the cells were labelled for 90 minutes with [$^3$H] leucine (1 µCi/0.5ml/well), and the trichloroacetic acid (TCA)-precipitable radioactivity was determined after incubating 30 minutes with cold 10% TCA, washing, harvesting the cells with 0.1M NaOH, neutralizing with HCl, and quantitating the radioactivity by liquid scintillation counting. The results show that $ppp(A2'p)_2A$, after the calcium-phosphate precipitation technique, resulted in a dose-dependent inhibition of protein synthesis. 50%-maximal inhibition occurred at approximately $10^{-9}$M 2-5A. However, the calcium phosphate treatment was very toxic to the cells, as determined from their morphology as well as approximately up to 40% reduction in protein synthesis of the cells receiving only the calcium phosphate treatment but no 2-5A. Cells that received all concentrations of 2-5A without addition of calcium phosphate coprecipitation showed no inhibition of protein synthesis.

DOTMA liposomes were prepared by drying DOTMA solutions in $CHCl_3$ to a film under a stream of nitrogen, removing residual solvent by placing under vacuum overnight, and then suspending in water with vigorous shaking and then sonicated in a bath type sonicator for 30 minutes. DOTMA liposomes were added to Vero cells in 24 well plates to give a final concentration of 0.015, 0.03, 0.06, or 0.12 mM DOTMA. Cells were incubated and protein synthesis was determined as described above except that the 60 mM $CaCl_2$ was not included. No significant inhibition of protein synthesis was obtained after 2 hours incubation. In another test, cells were incubated with samples for 2, 6, or 18 hours and protein synthesis was determined as described above. Samples were also included that contained a lipophilic derivative of 2-5A [5'-triphosphophoryladenylyl-(2'→5')adenylyl-(2'→5')adenylyl-(2'→6')(3'-aza-N-hexyl-1', 2',3',4'-tetradeo xyhexopyranos-1'-yl)adenine] prepared in the DOTMA liposomes in the following ratios:

0.03 mM DOTMA: $10^{-6}$M 2-5A analog;

0.06 mM DOTMA: $10^{-6}$M 2-5A analog;

0.012 mM DOTMA: $10^{-6}$M 2-5A analog.

When these preparations containing the 2-5A analog formulated in DOTMA liposomes were added to the cells, a significant inhibition of protein synthesis was obtained. After 6 hours incubation, the 2-5A analog alone at $10^{-6}$ M gave 82±14% of protein synthesis of untreated cells, DOTMA alone at 0.015, 0.03, and 0.06 mM gave 86±8, 80±6, and 77±4% of protein synthesis of untreated cells, whereas calcium phosphate alone gave 64±3% of protein synthesis of untreated cells. $10^{-6}$M 2-5A analog formulated in DOTMA at 0.015, 0.03, or 0.06 mM gave 23±7, 41±10, and 17±2% of protein synthesis of untreated cells. Thus the DOTMA formulation of the 2-5A analog served to introduce the 2-5A analog intracellularly, resulting in inhibition of cellular protein synthesis.

EXAMPLE 6

The ability to solubilize a drug is increased by use of the compounds and liposomes of this invention. In this way a greater concentration of a normally insoluble or sparingly soluble drug can be presented to the body.

For example, 1-[4-(4-chlorophenyl)-2-(2,6-dichlorophenylthio)-n-butyl] imidazole nitrate without the presence of any of the compounds of this invention is insoluble in aqueous buffer (phosphate buffered saline, pH 7.4).

A 0.3% soluble preparation of the above drug was prepared using the following method:

18 mg of 1-[4-(4-chlorophenyl)-2-(2,6-dichlorophenylthio)-n-butyl] imidazole nitrate and 482 mg of N-(2,3-di-( 9-(Z)-octadecenyloxy)-prop-1-yl-N,N,N-trimethylammonium chloride were dissolved in methylene dichloride. The methylene dichloride was evaporated under a stream of nitrogen and the dried film placed under vacuum overnight. The dried film was suspended in 6 ml phosphate buffered saline, pH 7.4, and sonicated to clarity.

EXAMPLE 7

DOTMA/DNA Complexes

This Example illustrates the formation of complexes between the liposomes made from compounds of Formula I and DNA.

DOTMA/DOPC vesicles were prepared by dissolving 10 mg DOTMA and 10 mg DOPC in chloroform and removing the solvent by drying under a stream of nitrogen gas. This dried film was placed under vacuum overnight to remove traces of solvent. This film was then suspended in 1 ml water with vigorous shaking and sonicated in a bath type sonicator for 30 minutes until clear producing DOTMA/DOPC SUV's at a concentration of 20 mg/ml total lipid.

Calf thymus DNA (obtained from Sigma Chemical Co.) was suspended in 5 ml water at a concentration of 1 mg/ml and sonicated in a bath sonicator for 30 min in order to reduce the size of the DNA strands.

The DNA was diluted with water to a concentration of 0.2 mg/ml. Liposome dilutions were made to give concentrations of 0.2, 0.4, 0.8, 1.2, 1.6, and 2.0 mg/ml lipid. Equal volumes of the DNA stock solution and each of the lip dilutions were mixed and observed for the appearance of aggregates. There was no aggregation in the samples with the highest and lowest lipid concentration. The samples at lipid dilutions of 0.8 and 1.2 mg/ml yielded large macroscopic aggregates. The 0.4 and 1.6 lipid dilutions gave turbid suspensions without microscopic aggregation or settling. Liposomes prepared without DOTMA or other compounds of Formula I did not form precipitates when mixed with DNA, indicating that in such cases a liposome/DNA complex did not form.

These results indicate that liposomes composed of DOTMA form a complex with DNA and that the precise nature of this complex is dependent on the molar ratio of DNA and DOTMA liposomes added.

EXAMPLE 8

Complex Absorption to Tissue Culture Cells

This Example demonstrates the interaction of DNA/DOTMA liposome complexes with tissue culture cells.

DOTMA/DOPC and DOTMA/DOPE vesicles containing rhodamine phosphatidylethanolamine were prepared by dissolving 10 mg DOTMA and 0.2 mg rhodamine phosphatidylethanolamine, with either 10 mg DOPC or 10 mg DOPE in chloroform and removing the solvent by drying under a stream of nitrogen gas. These dried films were placed under vacuum overnight to remove traces of solvent. The films were then suspended in 1 ml water with vigorous shaking and sonicated in a bath type sonicator for 30 minutes until clear producing DOTMA/DOPC and DOTMA/DOPE vesicles containing rhodamine-PE at a concentration of 20 mg/ml total lipid.

Calf thymus DNA (obtained from Sigma Chemical Co.) was suspended in 5 ml of water at a concentration of 1 mg/ml and sonicated in a bath sonicator for 30 min in order to reduce the size of the DNA strands.

The DNA was diluted to a concentration of 0.1 mg/ml and each of the liposome preparations was diluted to a concentration of 0.1 mg/ml and sonicated in a bath sonicator for 30 min in order to reduce the size of the DNA strands.

The DNA was diluted to a concentration of 0.1 mg/ml and each of the liposome preparations was diluted to a concentration of 0.6 mg/ml. 0.1 ml of the diluted DNA was added to 0.1 ml aliquotes of each of the diluted fluorescent liposome preparations. The samples were mixed to give the fluorescent DNA/liposome complexes.

Microscope slides containing 22×22 mm wells were seeded with 200,000 mouse fibroblast cells in each well. After 24 hrs the cells were washed with PBS and 1 ml of PBS was added to each well. 0.2 ml of each of the fluorescent liposome/DNA complexes was added to separate individual wells, the cells were incubated for 1 and 4 hours and observed, after washing, by fluorescence microscopy.

Based on the observed intense cell associated fluorescence it was apparent that the DNA/DOTMA liposome complexes readily and extensively associated with the cells. Negatively charged vesicles prepared from DOPC:DOPG, 7:3, or neutral vesicles, prepared from DOPC, and which do not contain DOTMA, do not readily adsorb to cells.

There was an additional difference between the cells exposed to complexes containing DOPC and those containing DOPE. With DOPC-containing complexes the majority of the fluorescence was punctuate and associated with the cell surface. With the DOPE containing complexes, the fluorescence was clearly associated with the interior the cell and after 4 hours there was an obvious ring of red fluorescence around the cell nucleus.

These results indicate that the DNA/DOTMA liposome complexes associate with tissue culture cells and that the precise way in which the complexes interact is critically dependent on both the presence of a compound of Formula I, as well as the other lipid component (DOPE vs. DOPC). DOPE showed special properties enabling the fluorescent components of the complex to enter the cellular cytoplasm and accumulate around the nucleus. This property can be advantageous for DNA delivery into cells.

EXAMPLE 9

Plasmid Transfection with DNA/DOTMA Liposome Complexes

This example demonstrates a method for efficiently introducing and expressing plasmids in eukaryotic cells. DOTMA/DOPC and DOTMA/DOPE vesicles were prepared by dissolving 10 mg DOTMA, with either 10 mg DOPC or 10 mg DOPE in chloroform and removing the solvent by drying under a stream of nitrogen gas. These dried films were placed under vacuum overnight to remove traces of solvent. The films were then suspended in 1 ml water with vigorous shaking and sonicated in a bath type sonicator for 30 minutes until clear, producing DOTMA/DOPC and DOTMA/DOPE SUV's at a concentration of 20 mg/ml.

The pSV2CAT plasmid was grown in *E. coli* (obtained from BRL, Bethesda Research Laboratory, Gaithersburg, Md., 20877), isolated and purified by procedures commonly known in the art and stored frozen in water at a concentration of 0.5 mg/ml. 0.05 ml of the plasmid was diluted into 0.935 ml of water and 0.015 ml of liposome stock was added to produce 1 ml of the DNA/DOTMA liposome complex.

500,000 mouse L929 cells were seeded onto 60 mm plastic petri dishes in tissue culture media containing 10% fetal calf serum. After 24 hours the cells were washed with PBS and 5 ml PBS was added. 1.0 ml of the freshly prepared plasmid DNA/DOTMA liposome complex was immediately added to each dish. The cells were incubated for 4 hours at which time 4 ml of the PBS was removed from each plate and replaced with media containing 10% fetal calf serum. For purposes of comparison one plate of cells was transfected by the standard calcium phosphate procedure well known to those familiar in the art, using 125 mM CaCl$_2$ and 7.5 mM phosphate to form the DNA precipitate, and performed according to methods reported in the literature (see, McKinnon and Graham in *Microinjection and Organelle Transplantation Techniques: Methods and Applications*, Eds. Celis et al., Academic Press, London, 1986). After 36 hours the cells were scraped off the plate, lysed and assayed for chloramphenical acyl transferase (CAT) activity (same reference) which is a measure of transfection efficiency by the pSV2CAT plasmid.

The data show that DNA/DOTMA liposome complexes prepared with DOPC gave transfection efficiencies comparable to the standard calcium phosphate procedure. The efficiency of transfection in the complexes containing DOPE was substantially greater than that of the standard calcium phosphate procedure.

EXAMPLE 10

Double Coated DNA/Lipid Complexes

This Example demonstrates the technique of coating the positively charged DNA/liposome complexes with a liposome of negative charge, in order to eliminate localized adsorption to cells.

DOTMA/DOPC SUV's were prepared by dissolving 40 mg DOTMA and 60 mg DOPC together in chloroform and removing the solvent by drying under a stream of nitrogen gas. This dried film was placed under vacuum overnight to remove traces of solvent. The film was then suspended in 2 ml water with vigorous shaking and sonicated in a bath type sonicator for 60 minutes until clear, producing DOTMA/DOPC vesicles at a concentration of 50 mg/ml.

DOPG/DOPC SUV's were prepared by dissolving 40 mg DOPG and 60 mg DOPC in chloroform and drying off the solvent under a stream of nitrogen gas. This dried film was placed under vacuum overnight to remove traces of solvent. The film was then suspended in 2 ml water with vigorous shaking and sonicated in a bath type sonicator for 30 minutes until clear, producing DOPG/DOPC SUV's at a concentration of 50 mg/ml.

The pUC8 plasmid (obtained from BRL, Bethesda Research Laboratory, Gaithersburg, Md., 20877) was grown in *E. coli*, isolated and purified by procedures commonly known in the art and stored frozen in water at a concentration of 1.0 mg/ml.

1 µl of pUC8 plasmid was added to 10 µl of the DOTMA/DOPC vesicles and thoroughly mixed by repeated passage of the sample through a 10 µl Hamilton syringe; then a 58 µl aliquot of DOPG/DOPC vesicles was added and the mixture was repeatedly passed through a 100 µl Hamilton syringe. When this preparation was run over a gel filtration column (Sephacryl S-1000) 100% of the DNA migrated with a different Stokes radius then the free untreated plasmid and the lipid fractions exactly overlapped with the DNA. This material does not interact with tissue culture cells.

This example demonstrates that a second coating of negatively charged lipid can be added to DNA/DOTMA liposome complexes to yield a product that has different properties than the starting material. This procedure results in essentially 100% entrapment of the DNA into the liposome complex.

EXAMPLE 11

Lectin Coupling to Double Coated DNA Complexes

This Example demonstrates the preparation of a DNA/liposome complex that specifically binds to selected cell types.

DOTMA/DOPC vesicles containing rhodamine-PE were prepared by dissolving 20 mg DOTMA, 30 mg DOPC and 0.5 mg in chloroform and drying off the solvent under a stream of nitrogen gas. This dried film was placed under vacuum overnight to remove traces of solvent. The film was then suspended in 1 ml water with vigorous shaking and sonicated in a bath type sonicator for 30 minutes until clear producing DOTMA/DOPC SUV's at a concentration of 50 mg/ml.

Maleimide-PE (chemical name: dioleoylphosphatidylethanolamine 4-(N-maleimidomethyl)-cyclohexanel-carboxylate) was prepared by mixing 17 mg succinimidyl 4-(N-maleimidomethyl) clyclohexane-1-carboxylate (SMCC), with 7 µl triethylamine and 25 mg dioleoylphosphatidylethanolamine (DOPE) in 2.5 ml of chloroform. The mixture was sealed tightly to prevent evaporation and stirred at room temperature overnight. The reaction mixture was washed, 3×2 ml, with 5% methanol in water. The chloroform was then dried over anhydrous sodium sulfate and the sample was applied to the top of a silica gel column (1×5 cm). The column was eluted with chloroform (5 ml), 5% methanol in chloroform (5 ml), 10% methanol in chloroform (5 ml), and finally 20% methanol in chloroform until all of the product was eluted. The fractions containing product were pooled and solvent removed on a rotary evaporator to give the 28 mg of maleimide-PE as white, oily residue. The material was estimated to be greater then 95% pure by thin layer chromatography on silica gel chloroform-methanolacetic acid (60:20:3) and was used without further purification.

DOPG/DOPC sonicated vesicles containing maleimide-PE were prepared by dissolving 16 mg DOPG, 24 mg DOPC and 0.4 mg maleimide-PE in chloroform and removing the solvent by drying under a stream of nitrogen gas. This dried film was then suspended in 0.8 ml water with vigorous shaking and sonicated in a bath type sonicator for 30 minutes until clear producing DOTMA/DOPC SUV's at a concentration of 50 mg/ml.

The pUC8 plasmid (obtained from BRL, Bethesda Research Laboratory, Gaithersburg, Md., 20877) was grown in *E. coli*, isolated and purified by procedures commonly known in the art and stored frozen in water at a concentration of 1.0 mg/ml.

10 µl of pUC8 plasmid was added to 100 µl of the DOTMA/DOPC vesicles and thoroughly mixed by repeated passage of the sample through a 100 µl Hamilton syringe; then a 580 µl aliquot of DOPG/DOPC vesicles containing maleimide-PE was added to the mixture and thoroughly mixed by repeated passage through a 500 µl Hamilton syringe.

The lectin, concanavalin A, was coupled to liposomes through the maleimide-PE moiety by a modification of published procedures (Martin F. T., Hubbell W. L. and Paphadjopoulos D., Biochemistry, 20, 4229 (1981); Leserman L. D., Machy P and Barbet J., in Liposome Technology, Vol III, ed. Gregoriadis G., CRC Press, Inc, Boca Raton, (1984)). 10 mg of concanavalin A in 3 ml PBS, pH 7.0 was reacted with S-acetyl-mercaptosuccinic anhydride (SAMSA; dissolved in dimethylformamide at 25 mM). Enough SAMSA was added to give a 50 fold molar excess of SAMSA over protein and the mixture was incubated at room temperature for 1 hour. The reaction mixture was dialyzed against 2×500 ml 0.1M sodium phosphate/0.1M sodium chloride/5 mM EDTA, pH 7.0. The dialyzate (approx. 3 ml) was reacted with 0.3 ml 1M hydroxylamine solution pH 7.5 for one hour at room temperature. Excess reagent was removed on a sephadex G-50 column (1×24 cm) equilibrated with 0.1M sodium phosphate/0.1M sodium chloride/5 mM EDTA/10 mM alpha-methylmannoside, pH 7, and maintained under an argon atmosphere. Free sulfhydryl per concanavalin A molecule was determined with 5,5'-dithiobis(2-nitro-benzoic acid), Ellman's reagent, and calculated to be 4 per protein molecule.

Conjugation of the sulfhydryl modified concanavalin A to the maleimide-PE containing, double coated, DNA/DOTMA lipid complexes was achieved by mixing 0.2 ml of the double coated DNA complexes containing maleimide-PE, with 2 ml of the concanavalin A (5.5 mg) and the vessel was capped under an argon atmosphere. The mixture was stirred at 4 degrees for three days and then passed through a sepharose 4B column (1.6×73 cm) equilibrated with 50 mM tris/50 mM NaCl/0.05% sodium azide/10 mM alpha-methylmannoside pH 7.0. The DNA/lipid complexes eluting in the void volume were pooled and dialyzed to remove alpha-methylmannoside. The dialyzed vesicles containing the conjugated concanavalin A were applied to tissue culture cells and observed by fluorescence microscopy.

B16/F10 tissue culture cells were seeded onto microscope slides containing 22×22 mm removable wells. After 24 hours the cells were washed with PBS and 1 ml of fresh PBS was added to each well. To half of the wells was added enough alpha-methylmannoside to give 5 mM and an aliquot of the rhodamine containing, concanavalin A conjugated, DNA/lipid complexes was added to each of the wells. The cells were incubated with the complexes for 1 hour at 37 degrees, washed with PBS and observed by fluorescence microscopy. The cells containing alpha-methylmannoside had significantly less fluorescence on their surface then the cells without the sugar.

This result indicates that DNA/DOTMA liposome complexes can be prepared which bind specifically to cells.

EXAMPLE 12

Synalar Efficacy in VC Screen

This Example demonstrates the efficacy of a DOTMA liposome solubilizing vehicle. The following results were obtained using the formulation described in Example 4, part 2.

Adult male and female volunteers were selected who did not receive any steroids and who did not participate in a study using steroids for at least four weeks prior to testing. The method was based on the Stoughton-McKenzie vasoconstriction assay for corticosteriod formulations. All preparations were placed in identical containers, coded and assigned by random tables to individual test sites. The forearms of the volunteers were prepared by gentle washing and drying. Strips of double adhesive coated BLENDER-M(Registered trademark) tape with 7×7 mm prepunched squares were applied to both forearms, so that each forearm had 32 application sites. A dose of the assigned formulation was applied to the skin in each square and spread evenly. A protective cage was placed over the sites on one arm for "open" application. On the other arm, the remaining backing from the Blenderm strips was removed and the application sites were occluded with SARAN WRAP(Registered Trademark). After six hours of exposure of the skin to the corticosteroid preparations, all the tapes were removed and the arms were washed. At 8, 24 and 32 hours after the time of application of the formulations two experienced observers independently scored the presence or absence of vasoconstriction and the degree of blanching on a scale of 0 to 3 under standard lighting conditions.

| | ASSAY SCORE (# of Sites Responding) | |
|---|---|---|
| Treatment | Occluded Assay | Open Assay |
| .01% Commercial Solution | 100 | 147 |
| .01% Commercial Cream | 210 | 112 |
| .1% DOTMA Solution | 159 | 150 |
| .03% DOTMA Solution | 189 | 138 |
| .01% DOTMA Solution | 178 | 125 |
| .003% DOTMA Solution | 175 | 78 |
| .001% DOTMA Solution | 130 | 60 |

The results of this experiment demonstrate that the DOTMA liposome/steroid formulation, which is prepared without the use of solvents or detergents, is as effective as the conventional formulations, which use potentially irritating solvents and detergents.

EXAMPLE 13

DOTMA Penetration into Mouse Stratum Corneum

This Example demonstrates the principle that DOTMA liposomes can be used to introduce drugs into and through the stratum corneum.

Sonicated liposomes in water were prepared containing 14 mM DOPC, 6 mM DOTMA and 0.2 mM rhodamine phosphatidylethanolamine. 0.01 ml of this preparation was applied to the mouse ear. After 30 min the mouse was sacrificed, the ear was dissected, prepared for cryostat sectioning and examined by fluorescent microscopy after sectioning. Fluorescent rhodamine-PE was observed to penetrate into the stratum corneum when DOTMA liposomes were used. When similar sonicated liposomes which did not contain DOTMA, were applied to the ear, the extent and pattern of observed fluorescence was very different. Only staining on the skin surface was observed; no penetration of fluorescence into the stratum corneum was detected. This lack of penetration was also observed when the dye was dissolved in either acetone or ethanol.

This result indicates that DOTMA liposomes can facilitate stratum corneum penetration of the rhodamine lipid, or a suitable biologically active medicament such as a lipophilic drug, peptides or proteins and the like.

EXAMPLE 14

Efficacy of DOTMA Vesicles as an Adjuvant

This Example demonstrates efficacy of DOTMA as an antigen carrier in subunit vaccines. This Example uses the formulation of Example 3, part 7.

Groups of 3 guinea pigs were given a single injection of infectious bovine rhinotracheitis viral antigen, derived from the membrane glycoprotein fraction of virus infected cells, in complete Freund's adjuvant at 100 mg antigen per guinea pig, or with 150 mg antigen in DOTMA/DSPC multilamellar vesicles (10 mg lipid/guinea pig) with or without 0.1 mg/guinea pig 6-O-stearoyl-N-acetylmuramyl-L-α-aminobutyryl-D-isoglutamine (6-O-stearoyl[Abu$^1$] MDP). The animals were bled at 0, 2 and 4 weeks after injection and the viral neutralizing antibody (reciprocal of endpoint dilution) in the serum was titered.

| SERUM NEUTRALIZING ANTIBODY TITER | | | |
|---|---|---|---|
| Treatment | 0 Week | 2 Week | 4 Week |
| Freund's Adjuvant | <5 | 128 | 125 |
| DOTMA liposomes | <5 | 130 | 130 |
| DOTMA liposomes + 6-O-Stearoyl-[Abu$^1$]-MDP | <5 | 115 | 129 |

These results demonstrate that the DOTMA liposomes are as effective as an antigen carrier as is complete Freund's adjuvant.

EXAMPLE 15

Use of DOTMA Vesicles to Achieve Local Skin Penetration of Interferon

This example demonstrates that DOTMA vesicles can be used to introduce large drugs, e.g., proteins, into the skin from a topical application. Sonicated liposomes containing the lipids as indicated below, at 30 mg/ml lipid and Azone® at 2:1 (lipid:Azone®) weight ratio or at 30 mM lipid (2:1 molar ratio, BISHOP/DOPE) were prepared in human or murine interferon-β solution (in water). Liposome-protein complex were applied topically to skin of hairless mice (0.01 ml per spot, 1 spot/sample/mouse, 2–3 mice/time point). $^{125}$I-human β-interferon was included in some preparations of human β-interferon to allow monitoring of uptake of interferon. Mice were sacrificed after 0, 2, 5, and 6 hours, and the skin area to which the liposome had been applied was washed with cotton swabs, excised, and the radioactivity of skin and cotton swab was quantitated in a γ-counter. The following results were obtained.

| Liposome Composition with $^{125}$I-Interferon | % $^{125}$I-Interferon Taken Up by Skin (Time, Hr)$^a$ | | | |
|---|---|---|---|---|
| | 0 | 2 | 4 | 6 |
| 1. None(free IFN) | 0.10 | 1.19 ± 0.04 | 0.50 ± 0.38 | 1.21 ± 0.36 |
| 2. DOTMA/ Azone® | 0.09 | 5.53 ± 3.89 | 8.03 ± 3.00 | 4.93 ± 3.44 |
| 3. BISHOP/ Azone® | 0.15 | 2.14 ± 1.28 | 2.51 ± 2.41 | 0.71 ± 0.52 |
| 4. BISHOP/ DOPE$^b$ | 0.16 | 0.68 ± 0.11 | 1.25 ± 0.47 | 0.65 ± 0.32 |

$^a$Mean ± S.D. of two mice; 0 hr sample, one mouse per sample.
$^b$ BISHOP = 2,3-Bis(hexadecyloxy)propyl-N,N,N-trimethylammonium chloride a.k.a., N-(2,3-dihexadecyloxy)-prop-1-yl-N,N,N-trimethyl-ammonium chloride;
DOPE = dioleoyl-L-α-phosphatidylethanolamine.

These results demonstrate that liposomes containing positively-charged lipids of Formula I promoted skin uptake of interferon.

To further assess this skin penetration by interferon, another test was conducted in which murine β-interferon-liposome complexes were incubated with mouse skin as above for 4 hours, mice were sacrificed and skin was washed and excised. Skin sections were frozen and thin sections prepared with a cyrostat. These sections were then incubated with rabbit IgG antibodies to murine interferon-β and washed. Second antibodies, FITC-labeled, against rabbit IgG were then added, incubated for an additional 30 minutes at 37° C., washed and tissue samples were analyzed under the fluorescent microscope. Tissue sections from mice originally treated with interferon complexed with Dotma:Azone® liposomes showed significant penetration of interferon through the stratum corneum. By contrast, tissue sections from mice originally treated with free interferon did not show any appreciable skin penetration of interferon.

EXAMPLE 16

Double Stranded RNA Entrapment Using the Methodology for Double Coated Complexes Commercially available (Beohringer-Mannheim) double stranded RNA (dsRNA) (poly IC) is very heterogenous with respect to size. This can be demonstrated by passing an aliquot of ds RNA dissolved in isotonic saline (0.9% sodium chloride, 50 mM HEPES, pH 7.0) over a gel filtration column (Sepharose CL-2B) equilibrated in the same buffer. Experiment 1 indicates that the double stranded RNA migrates in a very broad peak ranging between the void volume and the included volume of this column. Electrophoretic agarose gels likewise indicated a very heterogenous size distribution ranging between 100 and 3500 base pairs in length. However, we determined that sonication (2 hours, 15 degrees centigrade, in a sealed vial, using the inverted cup of a Branson 350 cell disruptor at the maximum setting) could educe the size of the dsRNA to about 130 base pairs. The gel filtration data for the sonicated dsRNA is also shown on Experiment 1. These results clearly indicate that the size of the dsRNA was reduced and the sample reached a more uniform size distribution than the starting material. Gel electrophoresis of the sample confirmed this conclusion and revealed that the resulting sample migrated with a size of about 130 base pairs compared to double stranded DNA.

A second experiment was done in order to determine whether any of dsRNA could be stably entrapped using a double coating procedure similar to the one described in Example 9. The sonicated dsRNA was mixed in a 1 to 10 weight ratio with positively charged DOTMA/DOPE liposomes by the usual methods described in example 8. The resulting solution contains DOTMA liposome/dsRNA complexes. This solution was mixed with a second solution of negatively charged liposomes (DOPG/DOPC) (1:1) so as to produce the double-coated dsRNA liposome complexes. The quantity of negatively charged liposomes exceeded the positively charged DOTMA liposomes by a factor of 10 so that the resulting complexes contained a net negative charge. These negatively charged dsRNA complexes were passed over the same gel filtration column. The data shown in Experiment 2 indicate that the free negatively charged liposomes (monitored by using a trace amount of $^{14}C$ labeled phospholipid during the liposome formulation) before complexation with dsRNA, migrate well into the gel filtration column. However, the same negatively charged liposomes, after complexation with dsRNA complexes, give rise to a different gel filtration pattern; approximately 30% of the lipid appears in the void volume, indicating that this fraction of the lipid is involved in a relatively large complex with the dsRNA. A similar fraction (i.e., 30%) of the dsRNA (monitored by using an assay employing ethidium bromide) is also involved in the high molecular weight complex, which is consistent with this conclusion. The void volume fractions containing the double coated negatively charged dsRNA complexes were pooled and rerun over the gel filtration column and all of the applied ds RNA and radioactive lipid migrated together in the void volume (data not shown). This result indicated that the double coated complexes were stable.

This example illustrates a convenient method, by simple mixing of premade liposome solutions, for the stable entrapment of a high percentage of polynucleotide into negatively charged complexes.

| Experiment 1, Example 16: Elution Profile of dsRNA from a Sepharose CL-23 Column | | | Experiment 2, Example 16: Elution Profile of dsRNA and Lipid Complexes from a Sepharose CL-2B Column | | | |
|---|---|---|---|---|---|---|
| | Percent Recovery | | | Percent Recovery | | |
| Fraction Number | Original RNA | Sonicated RNA | Fraction Number | Free [$^{14}$C]DOPG/DOPC | Double Coated Complexes RNA | [$^{14}$C]DOPG/DOPC |
| 1 |  | .564 | 1 | .065 | 540 | .041 |
| 2 | .108 |  | 2 | .044 | .540 | .030 |
| 3 | .075 | .564 | 3 | .073 | .216 | .041 |
| 5 | .075 | .564 | 4 | .077 | .513 | .041 |
| 6 | .075 | .564 | 5 | .052 | .540 | .041 |
| 8 | .075 | .564 | 6 | .089 | .540 | .038 |
| 9 | .345 | .564 | 7 | .085 | .540 | .046 |
| 10 | 2.073 | .564 | 8 | .081 | .216 | .024 |
| 11 | 2.829 | .580 | 9 | .134 | .405 | .212 |
| 12 | 3.207 | .590 | 10 | .955 | .945 | 3.112 |
| 13 | 3.639 | .661 | 11 | 1.166 | 7.297 | 5.272 |
| 14 | 4.341 | .800 | 12 | 1.227 | 9.459 | 3.250 |
| 15 | 4.665 | 1.040 | 13 | 1.296 | 5.540 | 1.988 |
| 16 | 5.097 | 1.451 | 14 | 1.439 | 3.243 | 1.446 |
| 17 | 5.745 | 2.177 | 15 | 1.727 | 1.891 | 1.446 |
| 18 | 7.041 | 3.048 | 16 | 1.882 | 1.351 | 1.663 |
| 19 | 6.987 | 4.322 | 17 | 2.146 | 1.486 | 1.826 |
| 20 | 7.365 | 5.741 | 18 | 2.471 | 1.621 | 2.170 |
| 21 | 7.851 | 7.354 | 19 | 2.951 | 1.756 | 2.537 |
| 22 | 7.905 | 8.870 | 20 | 3.841 | 1.891 | 3.008 |
| 23 |  | 9.935 | 21 | 4.886 | 2.162 | 3.548 |
| 24 | 6.555 | 10.758 | 22 | 6.345 | 2.432 | 4.669 |
| 25 | 5.691 | 10.774 | 23 | 8.139 | 2.972 | 6.033 |
| 26 | 4.287 | 10.435 | 24 | 10.060 | 3.783 | 8.179 |
| 27 | 3.909 | 9.290 | 25 | 12.077 | 4.729 | 10.245 |
| 28 | 2.397 | 7.629 | 26 | 11.865 | 5.945 | 11.278 |
| 29 | 1.749 | 6.300 | 27 | 9.674 | 6.891 | 10.110 |
| 30 | .885 | 4.290 | 28 | 7.536 | 7.297 | 8.292 |
| 31 | .669 | 2.870 | 29 | 4.890 | 7.837 | 5.578 |
| 32 | .237 | 2.000 | 30 | 2.817 | 6.486 | 3.247 |
| 33 | .291 | 1.322 | 31 | 1.300 | 5.135 | 1.716 |
| 35 | .129 | 1.032 | 32 | .654 | 3.378 | .829 |
|  |  |  | 33 | .422 | 2.027 | .432 |
|  |  |  | 34 | .247 | 1.297 | .201 |
|  |  |  | 35 | .195 | .810 | .151 |
|  |  |  | 36 | .138 | .945 | .107 |
|  |  |  | 37 | .121 | .675 | .107 |
|  |  |  | 38 | .105 | .000 | .099 |

EXAMPLE 17

Use of DOTMA to Increase Interferon Inducing Activity of dsRNA in Tissue Culture Cells Interferon treatment of various cells including both mouse and human cells results in induction of an enzyme, 2-5A synthetase, which when activated by double stranded RNA produces 2-5A. 2-5A is a polymer of ATP that contains unique 2'–5' linkages rather than the standard 3'–5' linkages. 2-5A is effectively a communication molecule which activates a latent 2'–5' endonuclease resulting in degradation of of cellular mRNA. In the absence of double stranded mRNA the 2-5A synthetase remains inactive, and no 2-5A is produced. In the presence of double stranded RNA, 2-5A is produced and can be produced in sufficient concentrations to degrade the majority of the cellular RNA, including ribosomal RNA, resulting in cell death. In this respect, this system can be used as cytotoxic assay to analyze the capacity of a compound to introduce double stranded RNA into the cytoplasm of a cell. The double stranded RNA commonly used is poly IC, a commercially available compound which is used experimentally and classically to induce interferon by methods well known to those familiar in the art. Poly IC will not penetrate cells and cause cytotoxic effects alone, but requires a vehicle to help carry it across the cell membrane. The most common agent used for this purpose is DEAE dextran in experimental cell culture systems and a complex of carboxymethyl cellulose and polylysine in clinical use. Both vehicles, however, are inefficient at introducing poly IC into the cell so that only a fraction of the cells are killed in an interferon induced cytotoxic assay. In addition DEAE dextran is itself toxic so that at concentrations where it acts effectively, it contributes significantly to the cellular cytotoxicity observed in experimental systems. An effective vehicle would allow high efficiency introduction of poly IC without contributing to cytotoxicity itself. The DOTMA lipid is such a vehicle. In experimental tests the frequency of surviving cells which have poly IC introduced by the DOTMA lipid is $1\times10^{-6}$. The DOTMA, when used under standard conditions, effectively introduces sufficient dsRNA into essentially every cell on a 10 cm² petri dish. The occasional surviving cells are not cells which merely have not received dsRNA, but rather have been mutants which are resistant to the cytotoxicity of dsRNA. These results indicate that the DOTMA lipid is an ideal vehicle for introducing double stranded RNA and other nucleic acids into cells.

TABLE I[a]

| Treatment | Cell Survival |
|---|---|
| Control | 100% |
| DOTMA/DOPE Liposomes (50 g/10 ml) | 100% |
| Poly IC (1 g/10 ml) | 100% |
| Liposomes + Poly IC | $1 \times 10^{-5}$% |

[a] 1 million mouse L-cells were seeded onto 10 cm² culture dishes in Eagle's minimal essential media (Gibco) containing 10% fetal calf serum. After 24 hours the cells were challenged with the treatments indicated in TABLE I. After an additional 24 hrs the cells were washed and stained with trypan blue to determine viability.

EXAMPLE 18

Comprehensive DNA Transfection Method

1. Introduction

A large body of work has demonstrated that under appropriate conditions, eukaryotic cells can take up exogenous DNA and that a portion of this DNA becomes localised in the nucleus. This phenomenon has been exploited in order to obtain both transient and stable expression of various genes. However, due in part to the size and charge of DNA and to the multitude of enzymatic and membrane barriers imposed by the cell, the spontaneous entry of intact DNA into the cell and its subsequent expression in the nucleus is a very inefficient process. For this reason, a wide variety of methods have been developed in order to facilitate this process. These methods include the use of polycations, calcium phosphate, liposome fusion, retroviruses, microinjection, electroporation, and protoplast fusion. However, all of these methods suffer from one or more problems related to either cellular toxicity, poor reproducibility, inconvenience or inefficiency of DNA delivery.

We have recently synthesize a cationic lipid which forms liposomes. We show here that these liposomes interact with DNA spontaneously, fuse with tissue culture cells and facilitate the delivery of functional DNA into the cell. The technique is simple, highly reproducible and more efficient than some other commonly used procedures.

2. Methods (A) Cells and Media

The cell line, COS-7 (ATCC CRL 1651) is a derivative of the simian kidney cell line CVI (ATCC CCL70) transformed with a mutant of SV40. ψ2 is a murine fibroblast cell line that stably expresses a packaging deficient retrovirus; it is used, most often, for the production of retroviral vector stocks. MSN610.2 is a glucocorticoid receptor deficient subclone of the mouse mammary tumor virus (MMTV)-invected, rat HTC derived cell line MSC.1. JZ.1 is a HTC cell line containing one integrated copy of MMTV. L-tkcells (ATCC CCL 1.3) are derived from murine L-cells and are thymidine kinase deficient. The TA1 cell line is derived from the murine fibroblast cell line 10t1/2. All cells were grown on plastic tissue culture plates in DMEM+10% foetal calf serum (f.c.s.) and in a 10% $CO_2$, 37° incubator except TA1 cells which were grown in BMEM+10% f.c.s. in a 5% $CO_2$, 37° incubator.

(B) DOTMA Synthesis and Liposome Preparation

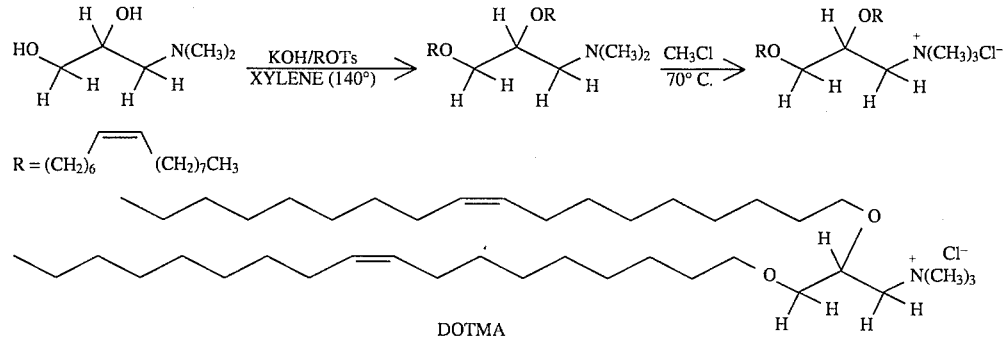

REACTION SCHEME V

DOTMA (N-(1-(2,3,-Dioleyloxy)propyl)-N,N,N-trimethylammonium chloride) was prepared as outlined in Reaction Scheme V. A mixture of 3-(dimethylamino)-1,2-propanediol (Aldrich Chemical Co., 1.19 g, 10 mmol), potassium tert-butoxide (3.36 g, 30 mmol) and oleyl p-toluenesulfonate (12.7 g, 30 mmol) in xylenes (50 ml) was stirred at room temperature and reduced pressure (30 Torr) for 30 min, and was then heated to 50° C. with stirring for an additional 15 min. The reaction vessel was purged with nitrogen, and the mixture was heated to reflux (approximately 140° C.) for 3 hrs. After cooling, the reaction mixture was diluted with hexane (100 ml), and the resulting solution was extracted with water (2×50 ml). The organic layer was concentrated, and the residue was chromatographed over silica gel by elution with a mixture of hexanes and ether (1:2) to afford the intermediate 2,3-dioleyloxy-1-(dimethylamino)-propane as a colorless oil. Quaternization was carried out by condensation of methyl chloride (50 ml) into a Parr pressure apparatus cooled to −78° C. containing this compound (10 g). The sealed vessel was heated behind a safety shield at 70° C. for 48 h. After cooling to 0° C., the reaction vessel was opened, and the excess methyl chloride was allowed to evaporate under a stream of nitrogen in a well-ventilated hood. The crude residue was recrystallized from acetonitrile to afford DOTMA as an off-white solid, mp. 35°–38° C. Full details of the synthesis of DOTMA and analogs will be published elsewhere (Gadek and Felgner, in preparation).

A solution of PE (10 mg) and DOTMA (10 mg) in chloroform (1 ml) was evaporated to dryness under a stream of nitrogen gas and residual solvent was removed under vacuum overnight. Liposomes were prepared by resuspending the lipids in deionized $H_2O$ (2 ml) and sonicating to clarity in a closed vial. Sterile preparations of liposomes are stable for at least 6 months at 4° C.

(C) Transfection of Cells using DOTMA (Lipofection)

Plasmid DNAs were purified by the method of Birnboim and Doly with subsequent removal of high Mr RNA by precipitation with 2.5M LiCl and banding on CsCl gradients. Plasmids pSV2CAT, pSV2neo. pZipneoSVX is a retroviral vector which encodes a neomycin resistance gene. pZipC5a and pMSGc5a are derived from pZipneoSVX and pMSG (Pharmacia) respectively by the insertion, in the anti-sense orientation, of a cDNA isolated recently from adipogenic cells (clone 5 from reference 17).

The details of individual transfections are given in the results section. A general protocol for transfections is given below.

(a) Formation of the lipid-DNA complexBoth DNA and lipid are diluted to 1.5 ml each with HBS (150 mM NaCl, 20 mM Hepes pH 7.4) and then mixed. The DNA lipid complexes form immediately. A typical transfection would use 1 to 10 µg DNA and 100 µg of total lipid (DOTMA:PE, 1:1).

(b) Treatment of cells—Just confluent 100 mm tissue culture plates of cells are washed 2× with 5 ml of HBS and 3 ml of the DNA-lipid solution is added. The cells are incubated for 3–5 hours at 37° and then 10 ml of DMEM +10% fcs is added. After incubation for 16 hours at 37° the medium is replaced with 10 ml fresh medium and cells are harvested by scraping 2–3 days later. Cell extracts were prepared and CAT assays performed as previously described. For stable transfections 50% confluent cells were treated as above except that 2 days after transfection cells were passaged and grown in selective medium for either neomycin resistance (0.4 mg/ml G418) or *E. coli* XGPRT expression.

(D) Transfection by Calcium Phosphate Precipitation and by DEAE-Dextran

Cells were transfected with calcium phosphate precipitated DNA as described with the addition of a glycerol shock. Similarly cells were transfected with the DEAE-dextran method as described.

(E) Staining of Cells with Rhodamine-Conjugated Lipid

A solution of DOTMA (10 mg), rhodamine-PE (Avanti Polar Lipids, Inc.; 0.2 mg) and either PE (10 mg) or PC (10 mg) in chloroform (1 ml) was evaporated to dryness under a stream of nitrogen gas and residual solvent was removed under vacuum overnight. Liposomes were prepared by resuspending the lipids in deionized $H_2O$ and sonicating to clarity in a closed vial. Fluorescent lipid-DNA complexes were prepared from these liposomes by mixing 0.5 ml of liposomes (0.1 mg/ml total lipid in HBS) and 0.5 ml of pSVCAT DNA (0.02 mg/ml in HBS). The complexes (5 µg) were added to mouse L-cells ($1 \times 10^5$) which had been seeded onto microscope slides containing 2 cm×2 cm wells. After a four hour incubation the cells were washed with HBS and examined by epifluorescence microscopy.

3. Results (A) Formation of DNA-Lipid Complexes

Cationic lipid vesicles might be expected to have the desirable properties of both cationic mediators of DNA transfection (e.g., spontaneous complex formation with DNA and the cell surface) and of liposome mediated transfection (rapid fusion and uptake of the DNA). However there are no widely available cationic, bilayer-forming lipids which give rise to physically stable liposomes. We, therefore, designed and synthesized a cationic lipid, DOTMA (Reaction Scheme V) which either alone or in combination with neutral phospholipids, spontaneously forms multilamellar liposomes which can be sonicated to form small unilamellar vesicles (not shown). The rectangular array of the parallel alkyl chains may be a significant factor contributing to the formation and stability of DOTMA bilayers as has been shown for other lipids. The characterization of these liposomes will be presented in detail elsewhere.

DNA interacts spontaneously with solutions of DOTMA to form lipid-DNA complexes. This complex formation is due presumably to ionic interactions between the positively charged group on the DOTMA molecule and the negatively charged phosphate groups on the DNA. Complex formation was examined using a sucrose density gradient (not shown). In the absence of lipid, DNA migrated to the bottom of the gradient while lipid, in the absence of DNA, floated at the top. When lipid was mixed with DNA at a ratio of 5:1 (wt:wt) all the DNA migrated with the lipid. The association of 100% of the DNA with DOTMA after gentle mixing contrasts with conventional liposome encapsulation procedures which usually entrap less than 10% of the DNA, require an additional purification step to remove unencapsulated DNA or involve potentially destructive conditions such as vigorous agitation or sonication.

(C) Fusion of DNA-Lipid Complexes with Cells

We speculated that the positively charged lipid, DOTMA, would not only interact with DNA to form a complex, but would also cause the complex to bind to tissue culture cells and possibly fuse with the plasma membrane. Incorporation of rhodamine conjugated phosphatidyl ethanolamine into the DNA-lipid complex allows one to follow the fate of the complex as it interacts with tissue culture cells. Fluorescence microscopy revealed that the complexes fuse with the cell membrane and diffuse throughout the intracellular membranes. Furthermore the intensity of cell associated fluorescence increased with time reaching a maximum after 4 hrs when virtually all the cells were fluorescently labelled. Our standard transfection cocktail contains DOTMA and a neutral lipid, phosphatidylethanolamine (DOPE), in a 1:1 (wt:wt) ratio (see materials and methods). The fusogenic capabilities of the complex can be controlled to a certain extent by the choice of the neutral lipid used to form the complex. The substitution of phosphatidylcholine for PE for instance, inhibits fusion of the complex with the cell membrane and a punctuate, surface associated fluorescence is seen on tissue culture cells. These results are what one might predict from the known fusogenic properties of DOPE.

(D) Optimization of the Transfection Protocol

Cells transfected with the plasmid pSV2CAT express CAT enzyme activity that can be measured in cell extracts 2 days after transfection. The lipid transfection technique was optimized for this kind of transient transfection assay using two monkey kidney cell lines CV1 and COS-7. COS-7 cells are often used for transient transfection assays as they produce SV40 T-antigen which allows replication of plasmids, such as pSV2CAT, containing an SV40 origin of replication. CV1 is the parental cell line which does not produce T-antigen and in which pSV2CAT cannot replicate.

(i) Concentration of DNA

Only 1 μg of pSV2CAT is required for the optimum transfection of COS-7 cells. Furthermore, transfection efficiency is relatively insensitive to a broad range of DNA concentrations (FIG. 1A); only a two fold difference in CAT activity is observed when 0.2 to 40 μg of pSV2CAT are used. In CV1 cells, maximal expression of CAT activity is achieved with 10 μg of DNA and there is a significant decrease with lower concentrations. In both CV1 and COS-7 cells very high DNA levels have some inhibitory effect. The difference in the dependence on DNA concentration between CV1 and COS-7 cells probably lies with the ability of COS-7 cells to replicate pSV2CAT to a high copy number. Presumably COS-7 cells are less dependent on the amount of DNA taken up by each cell than on the percentage of cells transfected. CV1 cells on the other hand would be dependent on both the amount taken up by each cell and on the transfection frequency.

(ii) Concentration of Lipid

Figure 1B:
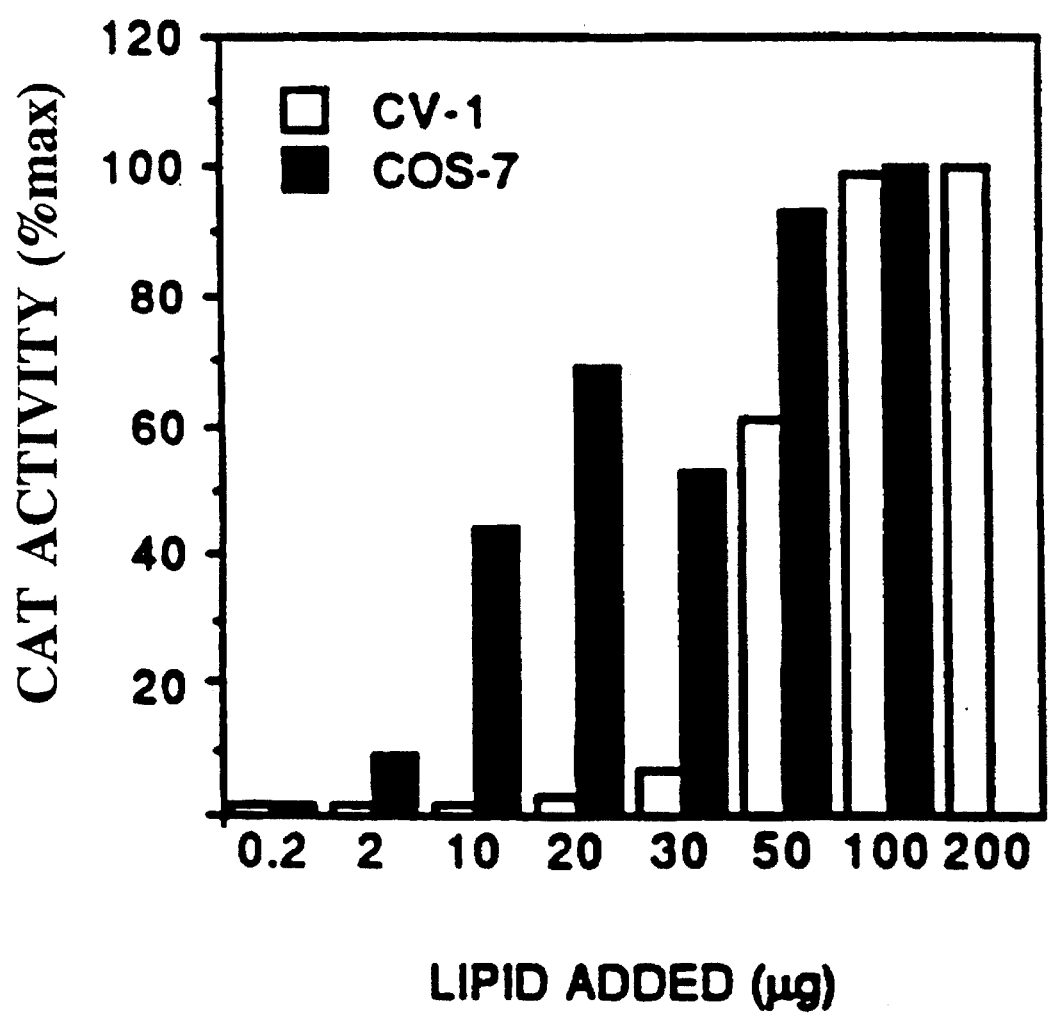
FIG. 1B is a bar graph of transfection efficiency as a function of lipic concentration.

Increasing concentrations of lipid improve transfection of both CV1 and COS-7 cells (FIG. 1B). However, the lipid is toxic to these cells at high levels (above 100 μg) and though an increase in specific activity of the cell extract can be obtained, the yield of enzyme activity decreases due to cell death. We have transfected a number of cell types which grow as monolayers and in every case satisfactory transfection was obtained using sub-toxic levels of lipid.

(iii) Time of Incubation with DOTMA:DNA Complexes

Figure 1C:
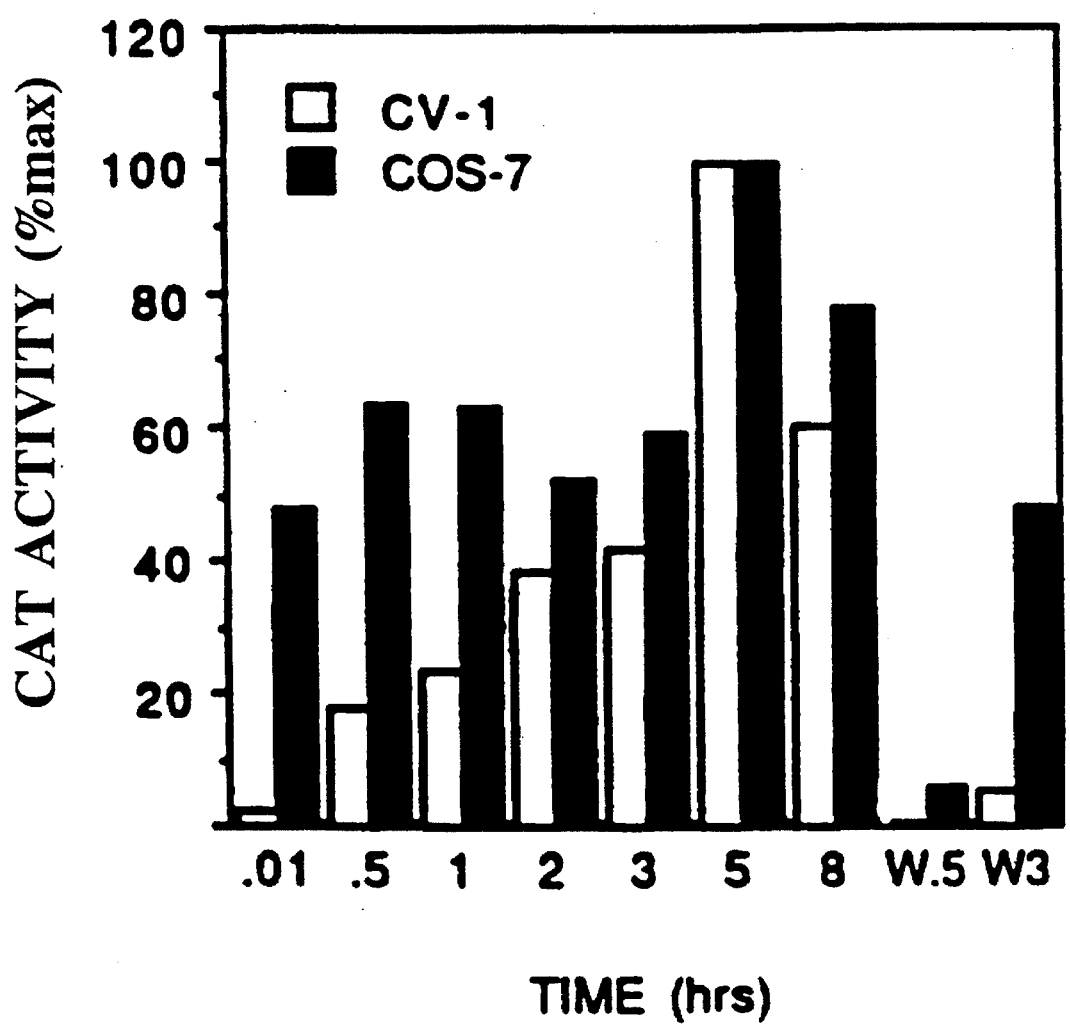
FIG. 1C is a bar graph of transfection efficiency as a function of incubation time.

In standard transfections cells were incubated with the lipid-DNA mixture for 3 hrs. Growth medium was then added to the cells and after a further 16 hrs this mixture was replaced with fresh medium. The length of the initial incubation period was varied and the results are presented in FIG. 1C. The addition of growth medium after 5 minutes of treatment of CV1 cells with the DNA-lipid mixture almost completely inhibits transfection. As the length of the treatment with the DNA-lipid complex increases, so does the transfection efficiency. An optimum transfection time of 5 hrs, was determined for both CV1 and COS cells and incubations of greater than 8 hr with lipid resulted in unacceptable levels of toxicity; this may vary however in other cell lines. Even after 3 hrs of treatment, however, replacement with fresh medium yielded only 7% of the CAT activity obtained when medium was added to cells in the continuing presence of the DNA:lipid complex (FIG. 1C). We have also observed that transfection of mouse L-cells with DOTMA is inhibited by serum-containing growth medium. In particular, when serum was present from the outset, CAT activity was reduced to less than 5% of control (data not shown). COS-7 cells, in contrast to CV1 and L-cells cells, appear partially refractory to the presence of serum-containing growth medium (FIG. 1C). Furthermore, washing the cells after 3 hrs of treatment with the DNA-lipid complex does not reduce the transfection efficiency, as measured by CAT activity, when compared to the addition of growth medium after 3 hrs. We suspect that the relative insensitivity of COS cells again reflects their ability to replicate pSV2CAT to high copy number.

(D) Lipofection vs DEAE-dextran and Calcium Phosphate for Transient and Stable Transfection of Cells The ability of DOTMA to facilitate DNA uptake and functional expression was compared with the commonly used mediators of transfection, DEAE-dextran and calcium phosphate. In CV-1 and COS 7 cells, DOTMA yielded a 6–11 fold increase in CAT activity relative to transient transfection with DEAE-dextran (Table 1). A variety of cell lines, including the rat hepatoma HTC cell line, seem to be highly refractory to transient transfection with DEAE-dextran. In contrast, DOTMA complexes of pSV2CAT yielded reproducible transfections of JZ.1 cells (a subclone of HTC cells) exhibiting at least an 80-fold enhancement over the DEAE-dextran procedure.

DOTMA is not only useful in transient assays but can also be used to facilitate the stable transformation of cells. We have analyzed the frequency of stable transfection of various cell lines using DOTMA and compared it to the frequency obtained using calcium phosphate precipitation of DNA (table 2). In four different cell lines, DOTMA yielded from 6 to greater than 80 times as many stable transformants using either neomycin (G418) resistance or *E. coli* XGPRT expression as the selectable markers.

3. Discussion

We have described the use of liposomes containing the cationic lipid DOTMA to facilitate the functional delivery of DNA into cells. The spontaneous formation of DNA-DOTMA complexes which are effective in DNA transfection suggests to us that a single plasmid is surrounded by sufficient cationic lipid to completely reverse the charge of the DNA and provide a net positively charged complex that would allow association with the negatively charged surface of the cell. The technique works well for both stable and transient expression of the introduced DNA and with several cell types we have studied it is more efficient than either DEAE-dextran or calcium phosphate precipitation.

The quantity of DNA required for an optimum signal in transient transfections varies with cell type. COS-7 cells which replicate pSV2CAT to a high copy number require only 1 μg of DNA while CV1 cells require 10 μg. In both cases DNA levels above the optimum are inhibitory although this effect is small. Indeed with COS-7 cells varying the DNA level from 0.2 to 40 μg gives a transfection signal which is never less than 50% of the maximum obtained. This, together with the observation that DOTMA-mediated transfection is effective for impure DNA preparations such as those obtained from 'mini-preps' would allow the rapid screening of new constructions by transfection. The smallest quantity of DNA required for a detectable signal depends to a large extent on the DNA and detection system used. With pSV2CAT in COS-7 cells 1 ng of DNA (without carrier) gives rise to an easily detectable CAT signal. Substitution of the SV40 early promoter with the Rous sarcoma viral promoter (pRSVCAT) allows CAT enzyme levels to be detected with as little as 0.1 ng of DNA (Northrop, unpublished). Moreover, with both pSV2CAT and pRSVCAT the addition of carrier DNA does not adversely affect the transfection signal obtained.

The concentration of lipid used in a transfection depends on the cell type. We have been able to obtain satisfactory transfection, both stable and transient with DOTMA:PE levels between 50 and 100 µg. Increasing the lipid concentration above these levels may increase the specific activity of the cell extract but significant toxicity also occurs. The toxicity varies with the type of cell, the duration of exposure to DOTMA, and also with the density of the cell culture; dense cultures are more resistant to the toxic effects of the lipid than less dense cultures. Although high levels of lipid are toxic, in our hands it appears to be less toxic than the concentration of DEAE-dextran which is required for optimum transfection of most cell types. Based on our experience it is best to optimize the various parameters described above for each cell line.

The exact composition of the DOTMA containing liposomes can be varied since pure DOTMA liposomes are almost as effective as DOTMA:PE (1:1) liposomes. If, however, the PE containing liposomes are formulated with a negatively charged lipid, such as phosphatidylglycerol, rather than with DOTMA, transfection is completely abolished. Surprisingly, two commercially available cationic lipids which bear significant structural similarity to DOTMA, stearylamine and dioctadecyl dimethyl ammonium bromide have shown little efficacy as mediators of DNA transfection with mouse L-cells (Felgner, unpublished). The properties of DOTMA containing liposomes we have described here suggest that this method may also have utility for introducing large DNA molecules, oligonucleotides, and RNAs into mammalian cells.

TABLE 1

Transient transfections: lipid compared with DEAE-dextran

| Cell Line | Lipid (µg) | DEAE-dextran (mg/ml) | Time (hrs) | DNA (µg) | CAT sp. act. (% max) |
|---|---|---|---|---|---|
| JZ.1 | 100 | | 3 | 5 | 19 |
| | 100 | | 3 | 25 | 100 |
| | 150 | | 3 | 25 | 80 |
| | | 0.25 | 5 | 5 | <1 |
| | | 0.25 | 5 | 25 | 1 |
| | | 0.25 | 16 | 25 | <1 |
| | | 0.50 | 5 | 25 | 1 |
| CV-1 | 100 | | 5 | 10 | 100 |
| | | 0.25 | 5 | 10 | 8.9 |
| COS-7 | 100 | | 5 | 1 | 100 |
| | | 0.25 | 5 | 1 | 7 |
| | | 0.25 | 5 | 10 | 16 |
| | | 0.50 | 5 | 1 | 7 |
| | | 0.50 | 5 | 10 | 11 |

Transfections were carried out as described in the Methods; lipid corresponds to DOTMA:PE (1:1). Each section of the table represents an independent experiment and in each case the transfection that yielded the highest level of CAT activity was set at 100%. All transfections were performed in duplicate and CAT assays from each were performed in duplicate.

TABLE 2

Comparisons of lipid and calcium phosphate stable transfections

| Cell Line | Plasmid | Transfection | Frequency ×10⁵ |
|---|---|---|---|
| L-TK | pSV2neo | CaCl₂ | 3 |
| | | Lipid | 45 |
| Ψ2 | pZIPSVX | CaCl₂ | 0.6 |
| | | Lipid | >49 |
| Ψ2 | pZIPC5a | CaCl₂ | 1.8 |
| | | Lipid | >68 |
| MSN610.2 | pSV2neo | CaCl₂ | 1.3 |
| | | Lipid | 8.2 |
| TA1 | pSV2neo | CaCl₂ | 2 |
| | | Lipid | 14 |
| TA1 | pZIPSVX | CaCl₂ | 0.7 |
| | | Lipid | 17 |
| TA1 | pMSGC5a | CaCl₂ | 1.3 |
| | | Lipid | 19 |

Cells were transfected with 7 µg of the indicated plasmid with no carrier DNA except for pSV2neo where 1 µg of plasmid with 10 µg of carrier DNA were used. The transfection frequency is the number of drug resistant colonies expressed as a fraction of the total number of cells plated.

What is claimed is:

1. An antigenic formulation, comprising:

an antigen; and a compound of Formula I:

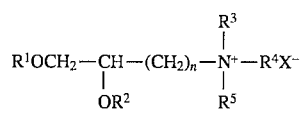

or an optical isomer thereof wherein $R^1$ and $R^2$ are the same or different and are an alkyl or alkenyl group of 6 to 24 carbon atoms; $R^3$, $R^4$ and $R^5$ are the same or different and are alkyl of 1 to 8 carbon atoms, aryl, aralkyl of 7 to 11 carbon atoms, or when two or three of $R^3$, $R^4$, and $R^5$ are taken together to form quinuclidino, pyrrolidino, piperidino, or morpholino; n is 1 to 8; and X is a pharmaceutically acceptable anion.

2. A formulation according to claim 1 wherein $R^1$ and $R^2$ are the same and are alkyl of 10 to 20 carbon atoms, $R^3$, $R^4$, and $R^5$ are methyl or ethyl, n is 1 to 4 and X is a halide ion.

3. A formulation according to claim 2 wherein n is 1.

4. The formulation of claim 3, wherein the compound of Formula I is (±) N-(2,3-di-(9-(Z)-octadecenyloxy))-prop-1-yl-N,N,N-trimethylammonium chloride or an optical isomer thereof.

* * * * *